(12) United States Patent
Prpa

(10) Patent No.: US 9,355,289 B2
(45) Date of Patent: May 31, 2016

(54) STERILE IMPLANT TRACKING DEVICE AND METHOD

(71) Applicant: Branko Prpa, Pleasant Prairie, WI (US)

(72) Inventor: Branko Prpa, Pleasant Prairie, WI (US)

(73) Assignee: Matrix IT Medical Tracking Systems, Inc., Racine, WI (US)

( * ) Notice: Subject to any disclaimer, the term of this patent is extended or adjusted under 35 U.S.C. 154(b) by 178 days.

(21) Appl. No.: 13/964,308

(22) Filed: Aug. 12, 2013

(65) Prior Publication Data

US 2013/0327836 A1   Dec. 12, 2013

Related U.S. Application Data

(63) Continuation-in-part of application No. 13/710,591, filed on Dec. 11, 2012, now Pat. No. 8,651,385, which is a continuation of application No. 13/437,161, filed on Apr. 2, 2012, now Pat. No. 8,430,320, which is a continuation-in-part of application No. 13/271,343, filed on Oct. 12, 2011, now Pat. No. 8,146,825.

(60) Provisional application No. 61/512,978, filed on Jul. 29, 2011, provisional application No. 61/492,177, filed on Jun. 1, 2011.

(51) Int. Cl.
*G06K 7/10* (2006.01)
*A61B 19/08* (2006.01)
*A61B 19/00* (2006.01)
*A61B 17/00* (2006.01)

(52) U.S. Cl.
CPC .......... *G06K 7/10821* (2013.01); *A61B 19/081* (2013.01); *A61B 19/44* (2013.01); *G06K 7/109* (2013.01); *A61B 2017/00902* (2013.01); *A61B 2019/442* (2013.01); *A61B 2019/448* (2013.01)

(58) Field of Classification Search
USPC ........................................................ 235/470
See application file for complete search history.

(56) References Cited

U.S. PATENT DOCUMENTS

| | | |
|---|---|---|
| D246,893 S | 1/1978 | Eron |
| D286,604 S | 11/1986 | Bierlein et al. |
| D288,766 S | 3/1987 | Tardif |
| 4,826,428 A | 5/1989 | Lam |
| D309,075 S | 7/1990 | Rossari |
| D322,391 S | 12/1991 | Morane |

(Continued)

FOREIGN PATENT DOCUMENTS

WO   2011033540   3/2011

OTHER PUBLICATIONS

Application Brief, Symbol DS6707-DP: Improve patient safety and workforce productivity through real-time accurate inventory counts in the operating room and beyond; motorola.com; Jan. 1, 2008.

(Continued)

*Primary Examiner* — Michael G Lee
*Assistant Examiner* — David Tardif
(74) *Attorney, Agent, or Firm* — Whyte Hirschboeck Dudek S.C.

(57) ABSTRACT

An assembly and method for tracking implant devices within a sterile field, the assembly comprising a reader that includes a housing structure with a base and a cover, a scanner having a scanner housing, where the scanner housing is at least partially positioned in a cavity provided in the base; and an aperture provided in the cover, where the cover is configured to receive a transparent sterile sheath to at least partially encase the cover.

23 Claims, 20 Drawing Sheets

(56) References Cited

U.S. PATENT DOCUMENTS

| | | | |
|---|---|---|---|
| D322,750 S | 12/1991 | Sommer | |
| 5,155,624 A | 10/1992 | Flagler | |
| 5,288,986 A | 2/1994 | Pine et al. | |
| D346,977 S | 5/1994 | Fiske | |
| D347,992 S | 6/1994 | Schmidt | |
| D351,338 S | 10/1994 | Koptis | |
| D356,044 S | 3/1995 | Clements | |
| 5,423,334 A | 6/1995 | Jordan | |
| D369,497 S | 5/1996 | Seddon | |
| 5,554,841 A | 9/1996 | Kost et al. | |
| D374,829 S | 10/1996 | Yue | |
| D378,057 S | 2/1997 | Dikowitz | |
| 5,631,456 A | 5/1997 | Kost et al. | |
| 5,653,938 A * | 8/1997 | Faries, Jr. | A61B 19/081 422/105 |
| D388,320 S | 12/1997 | Lamb | |
| 5,879,621 A * | 3/1999 | Faries, Jr. | A61B 19/081 422/105 |
| D410,399 S | 6/1999 | De Torfino | |
| D417,273 S | 11/1999 | Walker | |
| 6,026,328 A | 2/2000 | Peckham et al. | |
| 6,026,331 A | 2/2000 | Feldberg et al. | |
| 6,032,195 A | 2/2000 | Reber et al. | |
| D459,245 S | 6/2002 | Power | |
| D459,246 S | 6/2002 | Power et al. | |
| 6,729,546 B2 * | 5/2004 | Roustaei | G06K 7/10811 235/462.25 |
| D497,559 S | 10/2004 | Johnson | |
| D512,656 S | 12/2005 | Yeung | |
| D513,706 S | 1/2006 | Johnson | |
| D583,261 S | 12/2008 | Johnson et al. | |
| D596,299 S | 7/2009 | Han et al. | |
| 7,611,010 B2 | 11/2009 | Gammons | |
| D614,980 S | 5/2010 | Junes | |
| D614,981 S | 5/2010 | Junes | |
| D616,991 S | 6/2010 | Kitayama | |
| 7,813,809 B2 | 10/2010 | Strother et al. | |
| D629,525 S | 12/2010 | Ladwig et al. | |
| D630,756 S | 1/2011 | Kitayama | |
| D642,690 S | 8/2011 | Altmann et al. | |
| 2002/0000231 A1 | 1/2002 | McNeirney et al. | |
| 2002/0000234 A1 | 1/2002 | Manker et al. | |
| 2003/0069543 A1 * | 4/2003 | Carpenter | A61M 25/0084 604/190 |
| 2005/0203384 A1 | 9/2005 | Sati et al. | |
| 2006/0235488 A1 * | 10/2006 | Nycz | G06F 19/323 607/60 |
| 2006/0256400 A1 | 11/2006 | Carnevali | |
| 2006/0291533 A1 | 12/2006 | Faries et al. | |
| 2008/0015590 A1 | 1/2008 | Sanders et al. | |
| 2009/0247999 A1 | 10/2009 | Tuan et al. | |
| 2009/0317002 A1 * | 12/2009 | Dein | A61B 19/44 382/224 |
| 2010/0076306 A1 | 3/2010 | Daigneault et al. | |
| 2011/0023343 A1 | 2/2011 | Turner et al. | |
| 2011/0060386 A1 | 3/2011 | Woods et al. | |
| 2011/0114514 A1 | 5/2011 | Bagozzi et al. | |

OTHER PUBLICATIONS

Cognex, "Dataman logistics barcode readers", www.cognex.com/dataman500/. Jan. 1, 2012.

International Search Report and Written Opinion for PCT App. No. PCT/US2012/039980 mailed on Aug. 22, 2012.

Preliminary Report on Patentability mailed on Feb. 12, 2013 for PCT App. No. PCT/US2012/039980.

* cited by examiner

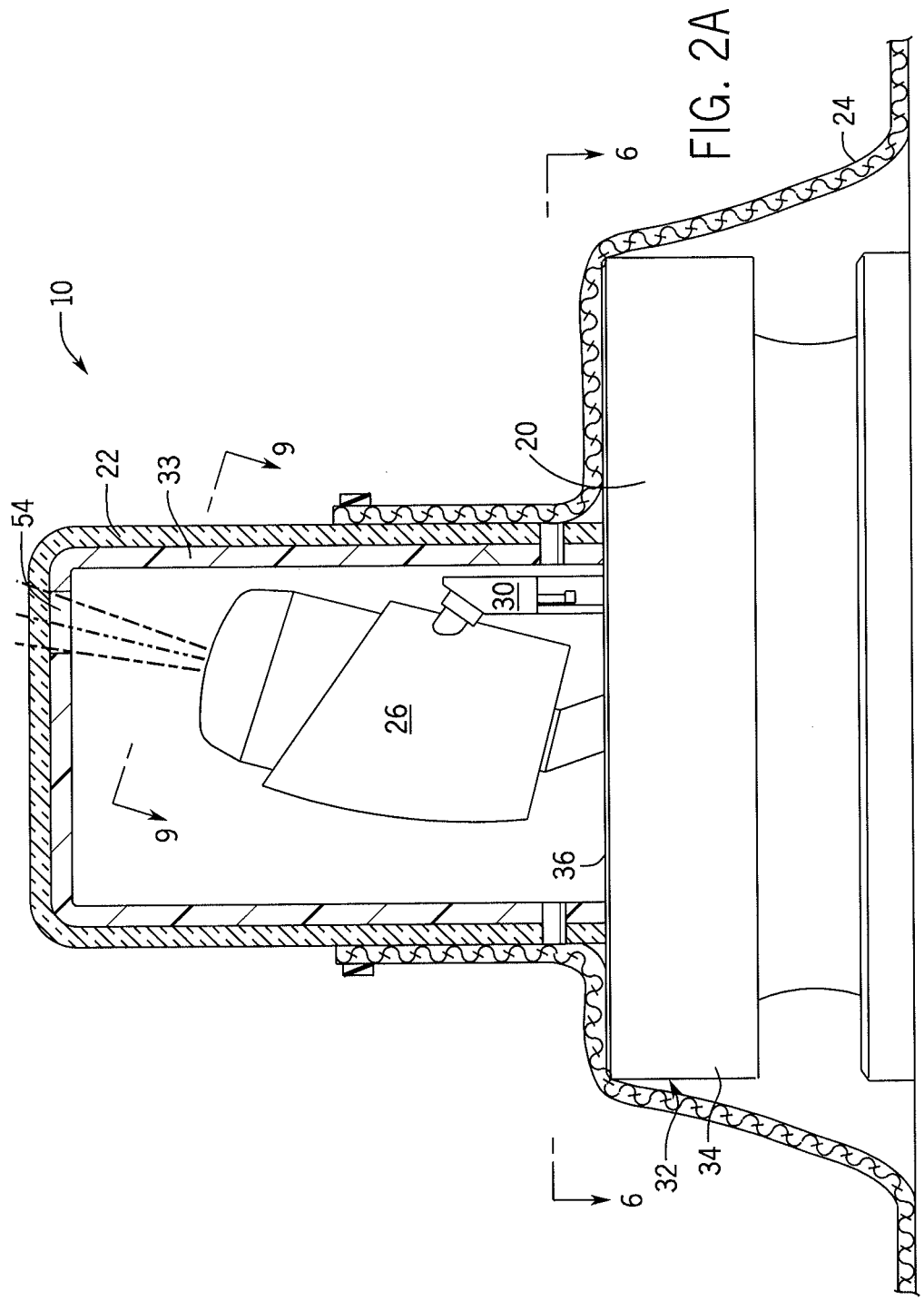

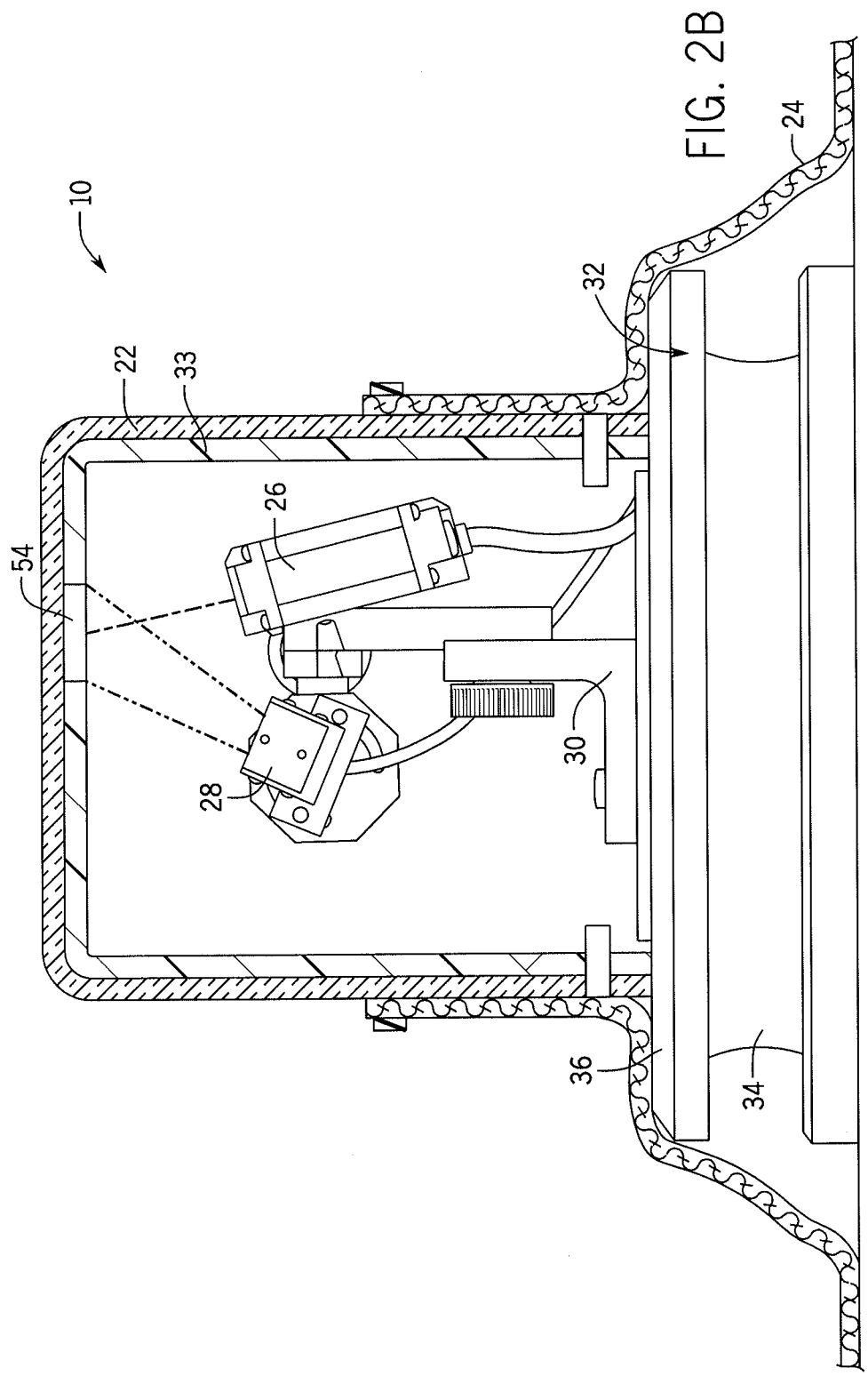

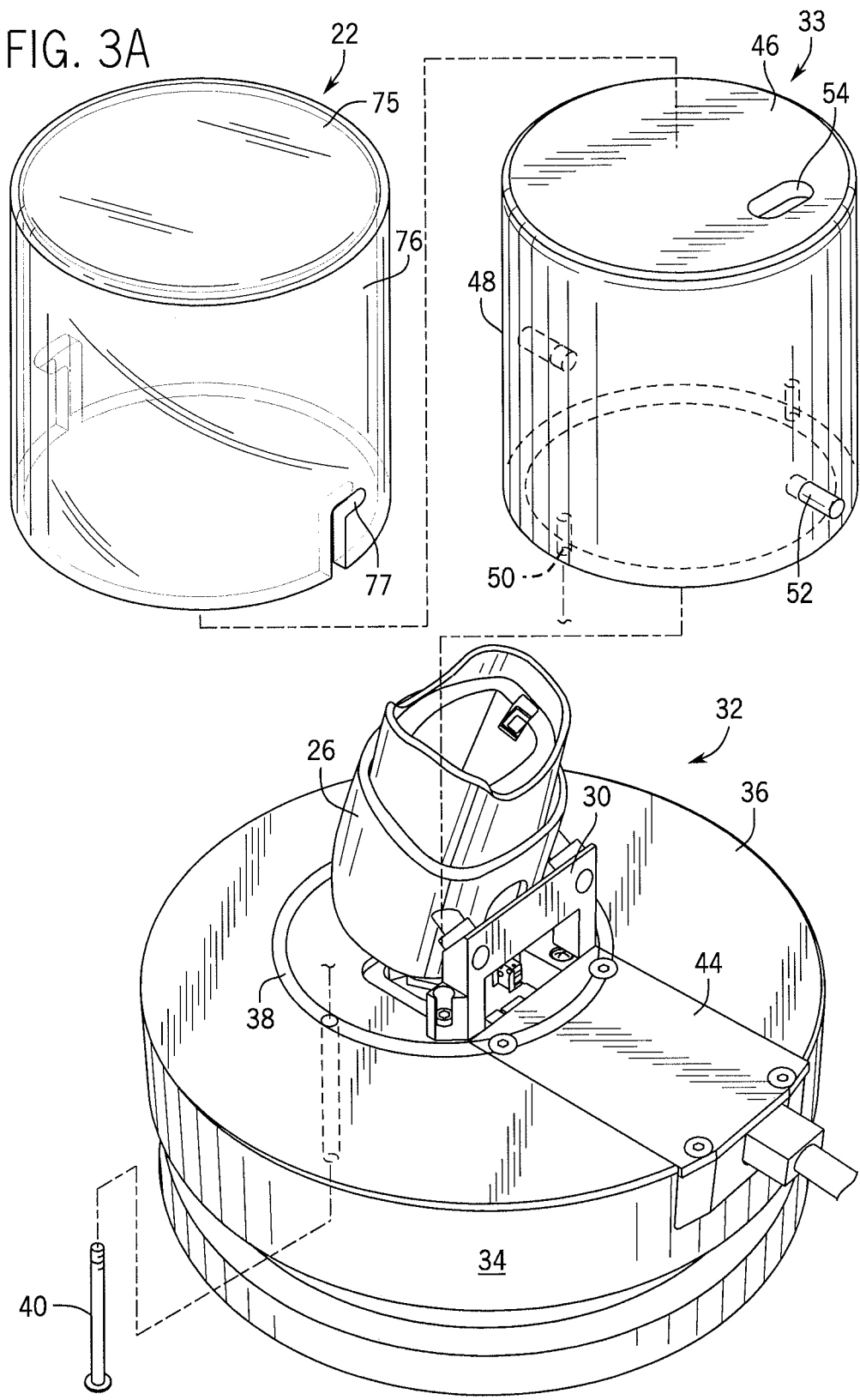

STERILE IMPLANT TRACKING DEVICE AND METHOD

CROSS REFERENCE TO RELATED APPLICATION

This application claims priority to and is a continuation-in-part of U.S. Nonprovisional patent application Ser. No. 13/710,591 filed Dec. 11, 2012 entitled "Sterile Implant Tracking Device and Method", which is a continuation of U.S. Nonprovisional patent application Ser. No. 13/437,161 filed Apr. 2, 2012 entitled "Sterile Implant Tracking Device and Method", which is a continuation-in-part of U.S. Nonprovisional patent application Ser. No. 13/271,343 filed Oct. 12, 2011, which claims the benefit of U.S. Provisional Patent Application No. 61/512,978 filed on Jul. 29, 2011 and U.S. Provisional Patent Application No. 61/492,177 filed on Jun. 1, 2011, the entire content of each application is incorporated by reference herein.

BACKGROUND OF THE INVENTION

1. Field of the Invention

This invention relates to an implant tracking system using an optical-based identification technique.

2. Description of the Related Art

Tracking and managing orthopedic implant replacements is an important health issue. Typically each implant contains a unique identification number, such as, for example, a manufacturer's identification and/or serial number. Whenever an implant is placed, this number is recorded as a permanent record in a database. In the future, this number can be referenced to track the age of the implant, the manufacturer for purposes of recall and adjustment, and can be used postmortem to identify a person having the implant.

The unique identification number may be tracked by identifiers, such as unique labels or other indicia, applied to the product and/or packaging, and the labels may remain associated with the implant until the implant is used. In some cases, product labels include adhesive portions that can be applied to a chart or file of a patient to conveniently associate the medical device with a particular patient.

The numerical values and ranges in this disclosure are exemplary and therefore can be adjusted to include lower or higher values and ranges as necessary to provide the intended operation of the various embodiments of the sterile implant tracking device and method.

Identifiers may be any graphic that is capable of retaining identifying information. In some embodiments, the identifier is a one or two dimensional bar code suitable for scanning by an optical scanner such as a bar code reader. The identifier may be a two dimensional (2D) etched matrix of 2 millimeters (mm) by 2 mm (2×2 mm) or 1.4 mm by 1.4 mm (1.4×1.4 mm). The identifier may also be a radio frequency identification tag that is readable through radio frequency transmission generated by an independently powered RFID device. The identifier may also be an RFID tag that includes a transponder and is readable in response to a radio frequency signal transmitted to the RFID device. In some embodiments, the identifier is a human readable visual and/or tactile graphic such as alphanumeric characters that can be manually recorded in a database or chart.

It would be beneficial if physicians were able to obtain additional information about an implant and/or a patient from an implant identifier such as the manufacturer and model number of the device, the serial number of the device, the treating physician's name and contact information, and the patient's name, contact information, medical condition and treatment, among other relevant information.

Currently, difficulty arises in tracking medical implants. For example, medical implants are difficult to track because the implants generally do not have adequate surface area for applying marks. Thus, in many instances, implants are not tracked beyond their manufacturing facility, and may only be counted when reconciled for payment as one of many products that were not returned to a manufacturer for replenishment.

There is a strong and growing need to not only track medical implants but to do so efficiently while maintaining a sterile operating environment. Therefore, if the tracking system involves a reader, such as a barcode scanner or RFID reader, then the reader itself needs to be sterile so as not to contaminate the medical implant of which it is reading or the personnel operating the reader.

Medical equipment may be sterilized by the use of chemical or physical agents, for example using hot steam, gas or gamma rays sterilization. However, these means may not be appropriate for more delicate medical equipment, such as a reader.

There exists a need for a sterile interface for use with a reader that allows for the efficient use of the reader in a sterile operating room environment.

SUMMARY

In an embodiment, the invention is an assembly for tracking implants comprising a (i) reader, (ii) medical drape, and (iii) computer. The reader comprises a (a) scanner, (b) housing structure comprising a cover and base, and optionally (c) transparent sterile sheath having a top surface and side walls and encases the cover of the housing structure. The cover has an aperture through the top surface of the cover. The medical drape is attached to the side walls of the transparent sterile sheath. The computer is in communication with the reader.

In an embodiment, the invention is a reader comprising a scanner, a scanner mounting structure supporting the scanner, a housing structure comprising a cover and base, and an optional transparent sterile sheath encasing the cover of the housing structure. The base comprises a top surface to receive the scanner mounting structure, an inset groove to receive the cover, an inset channel extending radially from the cover to the edge of the top surface of the base, and a removable channel cover. The scanner mounting structure is attached to the base, and both the scanner and mounting structure are enclosed in the housing structure.

In an embodiment, the invention is a method of using a reader comprising the steps of providing a reader, placing an implant having an identifier onto the top surface of the transparent sterile sheath above the aperture, and scanning the identifier of the implant to electronically record the stored data.

In an embodiment, the invention is a tracking assembly comprising a reader comprising, a housing structure that includes a base and a cover, a scanner having a scanner housing, where the scanner housing is at least partially positioned in a cavity provided in the base; and an aperture provided in the cover, where the cover is configured to receive a transparent sterile sheath to at least partially encase the cover.

In an embodiment, the invention is a tracking assembly comprising, a reader comprising, a scanner; a scanner mounting structure supporting the scanner; a housing structure that includes a cover with an aperture on a top surface of the cover and a base secured to the cover, where the housing structure is configured to receive a one or more coverings to at least partially enclose the housing structure, where the scanner mounting structure is secured to the base, and where the scanner and scanner mounting structure are substantially enclosed in the housing structure.

In an embodiment, the invention is a method of using a tracking assembly comprising the steps of: providing a tracking assembly comprising a reader that includes a scanner and a housing structure with a cover having an aperture on a top surface; covering the cover with a transparent sterile sheath; placing an implant having an identifier over the aperture; and scanning the identifier of the implant to electronically record the implant data.

BRIEF DESCRIPTION OF THE DRAWINGS

The invention is described generally with reference to the drawings for the purpose of illustrating certain embodiments only, and not for the purpose of limiting the scope of the invention. In the drawings, like numerals are used to designate like parts throughout the same.

FIG. 2A is a sectional view of the assembly of FIG. 1.

FIG. 2B is a sectional view of an embodiment of the assembly of FIG. 1.

FIG. 3A is an exploded view of the reader of FIG. 1.

DETAILED DESCRIPTION

The present disclosure provides a system for tracking implants (e.g., screws, plates, cages, nuts, rods, etc.). An advantage of the present method for tracking an implant is a vast improvement in sterility and efficiency over current tracking methods. Typically, in an operating room, the patient to receive the implant is lying on an operating table in the center of the room. There is a sterile field extending two to three feet radially from the operating table. The present assembly comprising a reader assembled with transparent sterile sheath and sterile medical drape may be inside the sterile field. A computer, in communication with the reader, is typically outside the sterile field and, in certain instances, operated by a person outside the sterile field. The operator of the computer can log into the software which is password protected as the surgery is beginning and input certain information such as the patient's name, etc., to save time.

The present method increases efficiency in the operating room by decreasing the time spent during operation on scanning and tracking every implant going into the patient while maintaining a sterile environment. For example, during spinal surgery, the surgeon requests numerous screws, plates, hooks, and cages, and each implant must be tracked by recording its manufacturer's information, lot number, serial number, etc., in addition to where that screw is implanted in the spine. Using the present assembly, the surgeon would request a screw, for example, having an identifier on its surface. The assistant would take the screw out of the sterile package and set the screw down on top of the transparent sterile sheath above an aperture on the reader. The reader would beep to indicate a successful scan of the identifier, and the assistant would hand the screw to the surgeon for implantation. The information (manufacturer's information, lot number, serial number, etc.) obtained from the identifier by the reader is transferred to the computer and the user of the computer can input data that indicates where the screw was implanted according to the surgeon's instruction. The location data of where the implant is placed in the patient may be aided by the software, which pulls up an anatomical image where the user of the computer can then just select visually where the implant was inserted.

Table Top Implant Tracking Assembly

Figure 1:
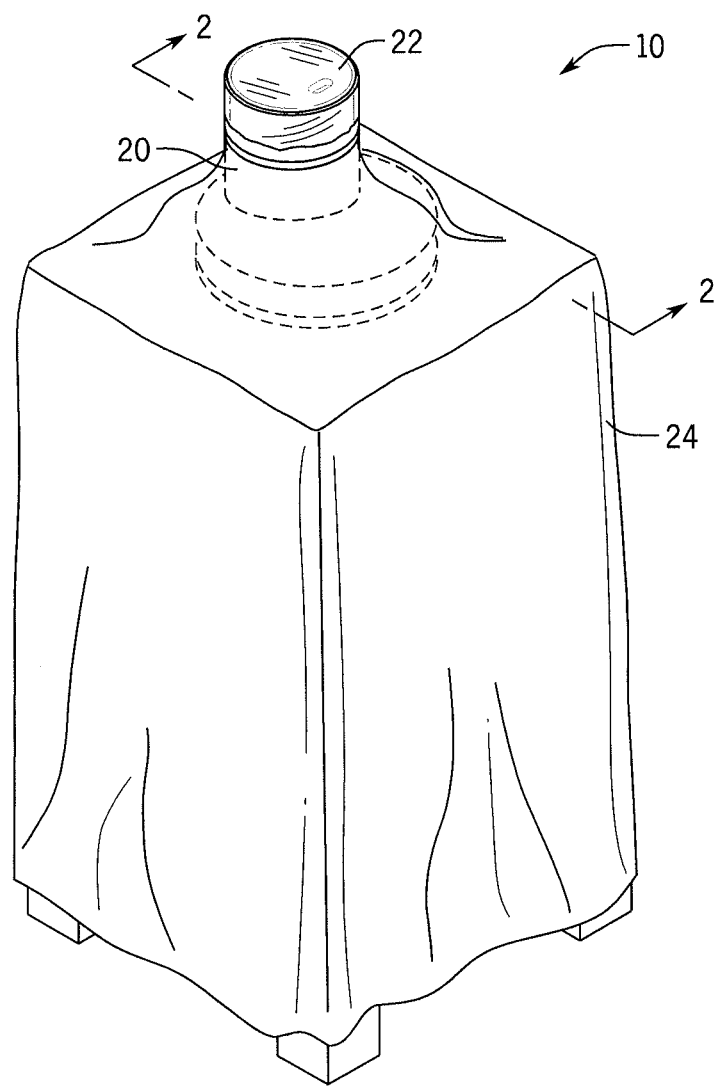
FIG. 1 is a schematic of an assembly of an embodiment of the invention including a reader and medical drape.

FIG. 1 depicts an embodiment of an implant tracking assembly 10 which includes reader 20 and medical drape 24. FIG. 1 shows reader 20 comprising an optional transparent sterile sheath 22 that fits, preferably snugly, over the top surface of reader 20. Assembly 10 includes medical drape 24 which is temporarily attached to and extends radially from the side walls of the transparent sterile sheath 22 to cover the remaining elements of the reader, such as possible electrical cords and control panels, among other things. Assembly 10 includes a computer 25 (not shown) in communication with reader 20. Although FIG. 1 shows reader 20 placed on a table, the table is not part of the assembly 10. The reader device in assembly 10 may be a table top reader, a handheld reader, or a table top-handheld reader. The implant tracking assembly 10 can include one or more coverings to provide limitation of contaminants to and/or from reader 20, where the one or more coverings can include the transparent sterile sheath 22 and medical drape 24.

Table Top Reader

FIG. 2A is a sectional view of reader 20. Reader 20 includes scanner 26, scanner mounting structure 30, and housing structure 32 including cover 33 and base 34. As seen in FIGS. 2A-4, base 34 of housing structure 32 includes a base top surface 36 to receive the scanner mounting structure 30, and inset groove 38 to receive the bottom edge of cover 33. One or more vertical pins 40 may extend up from the bottom of the base through the inset groove 38. The shape of the base may be circular as shown in FIG. 1, but as one skilled in the art would understand, the disclosure is not limited to a circular base. In addition, in at least some embodiments, base 34 includes a diameter DI that extends between about 6 inches to about 10 inches. Further, base 34 can weigh between about one pound to about four pounds. FIG. 2A shows an embodiment where the base has a track creating a lip or shelf that allows for easy transport or mobility of the reader by a user inserting their fingers into the track and picking up the reader. Further, cover 33 and base 34 can be integrally formed, although the separability of cover 33 and base 34 can allow for insertion/installation of various components inside housing structure 32, in at least some embodiments, an alternate access may be provided to facilitate access for insertion of one or more components therein if cover 33 and base 34 are integrally formed.

FIG. 3A is an exploded view of housing structure 32 and transparent sterile sheath 22. Housing structure 32 further includes cover 33. Cover 33 includes cover top surface 46 and side wall 48, as seen in FIG. 3A. In an embodiment, cover top surface 46 is circular and thus the side wall 48 is in the shape of a cylinder. Alternatively, cover top surface 46 may be square or rectangular, yielding four side walls 48. Side wall 48 may have at least one radial pin 52 extending radially out from the side wall 48. The cover top surface 46 has an aperture 54 that may be circular, oblong, square, or any other shape that allows the reader device to properly scan a medical implant placed above aperture 54. Side wall 48 may have at least one pin hole extending vertically into side wall 48 to receive vertical pin 40. Equivalents of pins are screws, bolts, nails, etc. In an embodiment, cover 33 is engaged with inset groove 38 of base 34 and vertical pin 40 is engaged with pin hole 50 of cover 33, securing cover 33 from any lateral movement. Cover 33 may sit in the center of base 34 or, more preferably, off center.

Housing structure 32 is made of an opaque material such as from a dense molded plastic, preferably a dark color, more preferably black. Utilizing a darker color can serve to reduce light noise, such as reflections of light, which can hinder the reader's ability to provide effective scans. Although in at least some embodiments, one or more portions of housing structure 32 can be comprised of materials other than plastic, as well as lighter colors.

Figures 4, 5:
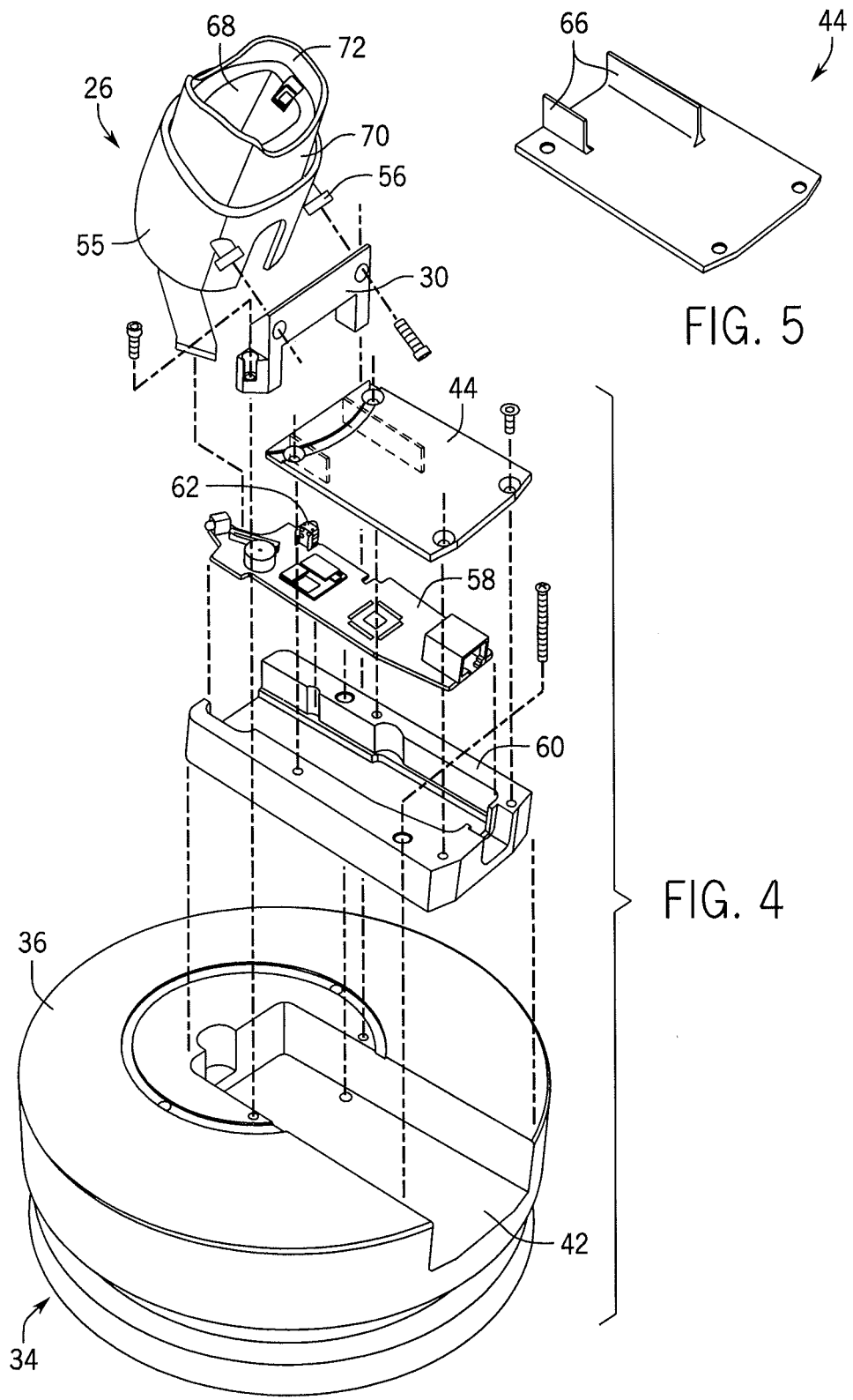
FIG. 4 is an exploded view of the reader of FIG. 3A without the cover.
FIG. 5 is a bottom view of the removable channel cover.
Figure 10:
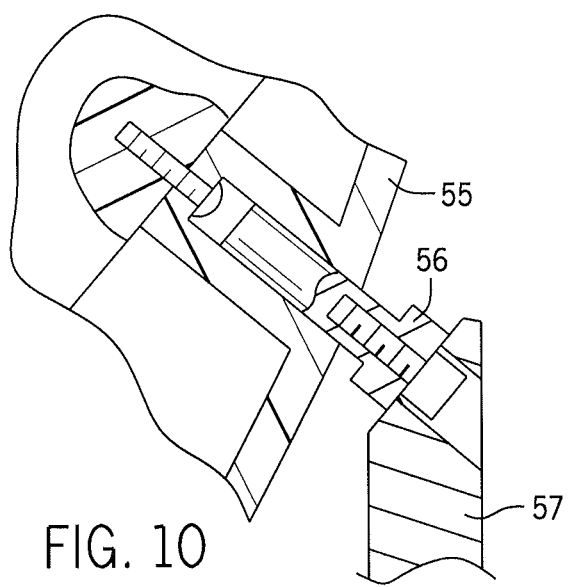
FIG. 10 is a sectional view of FIG. 9.

FIG. 4 is an exploded view of base 34, scanner mounting structure 30, and scanner 26. In an embodiment, scanning mounting structure 30 is bolted or otherwise securely fastened to a top surface of removable channel cover 44. Alternatively, scanning mounting structure 30 is bolted to base top surface 36 of base 34. Scanner 26 is housed in scanner housing 55, which is attached to scanning mounting structure 30 by screws that are received into receptacles 56 of scanner housing 55 (see FIG. 10). The position of scanner 26 is locked on the focal point of scanner 26, which is 1-3 millimeters (mm), preferably 1-2 mm, above the top surface of cover 33 in the area above aperture 54. When reader 20 comprises transparent sterile sheath 22, the focal point is on the surface of transparent sterile sheath 22 in the area above aperture 54. Alternatively, scanner 26 may be manufactured with adjustable knobs to allow a user to manually adjust the position of the scanner for an optimal read, as shown in FIGS. 2B and 3B.

Figure 3B:
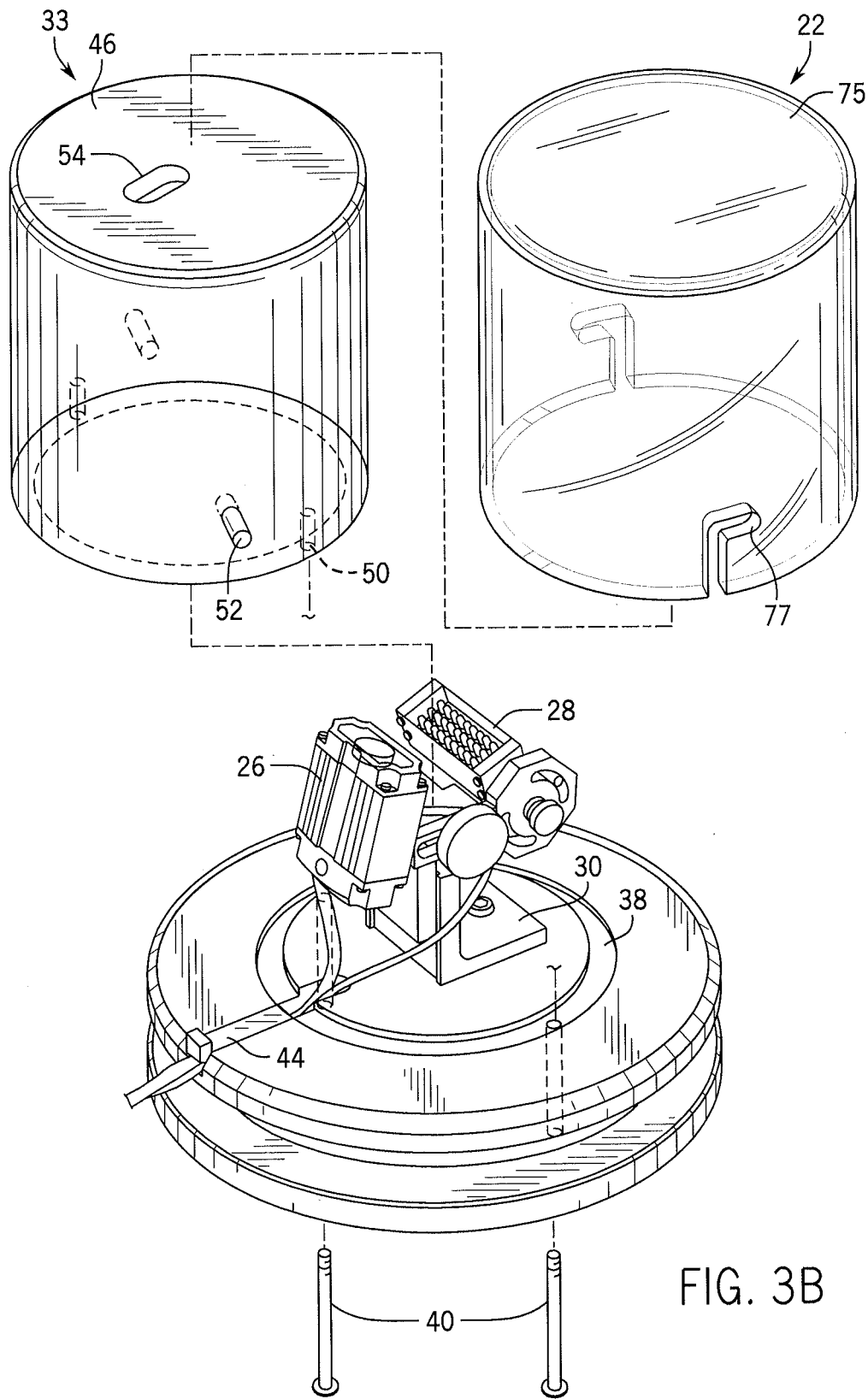
FIG. 3B is an exploded view of an embodiment of the assembly of FIG. 1.

Base 34 includes an inset channel 42 extending radially from the scanner mounting structure 30 to the edge of base 34 where the electrical cords from scanner 26 lie in inset channel 42 and extend out to a power source, control panel, or other appropriate source, as shown in FIG. 3B. Preferably, as shown in FIG. 4, inset channel 42 houses circuit board 58 which is in communication with scanner 26 and computer 25, typically, via electrical cords or wirelessly. In an embodiment, circuit board 58 is equivalent to the circuit board found in Motorola Symbol DS6707-DP.

Figure 7:
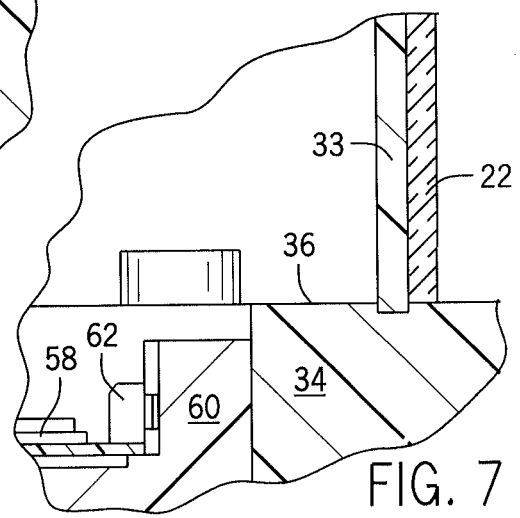
FIG. 7 is a sectional view of FIG. 6.

Circuit board 58 is securely positioned in inset channel 42 in circuit board mold 60. Circuit board mold 60 is designed such that the outer surface matches the shape of inset channel 42 and the inner surface matches that of the shape of circuit board 58. Circuit board mold 60 is secured to base 34 by screws or pins and removable channel cover 44 is secured to circuit board mold 60 by screws or pins. In an embodiment, circuit board 58 comprises button 62, which activates scanner 26 to take a scan upon depressing button 62. The inner surface of circuit board mold 60 is designed such that when circuit board 58 is positioned in circuit board mold 60, button 62 is constantly depressed into the "on" position, which can be seen in FIG. 7.

Figure 6:
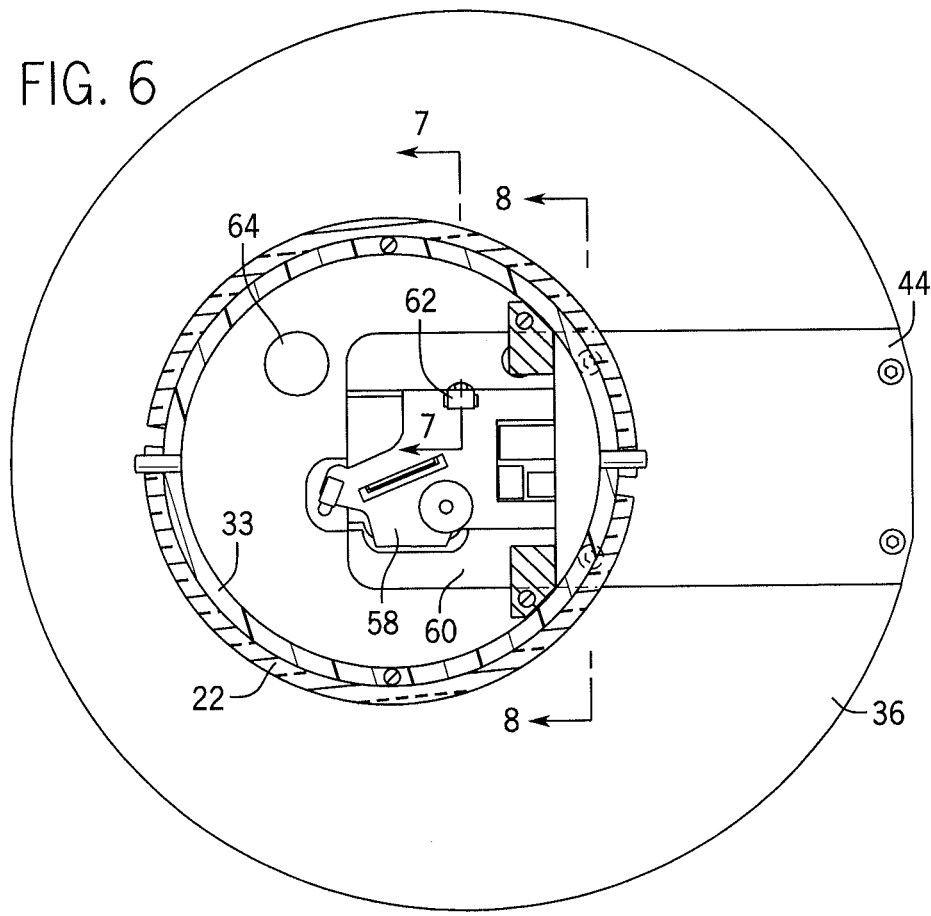
FIG. 6 is a sectional view of the reader of FIG. 2A.
Figure 8:
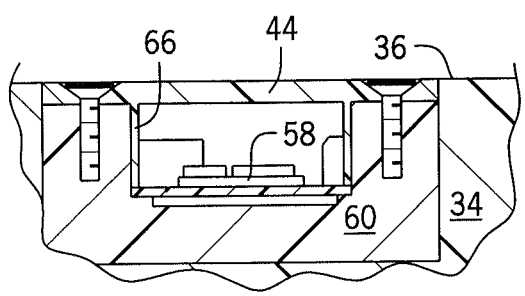
FIG. 8 is a sectional view of FIG. 6.

Removable channel cover 44 is designed such that when in place it is merely a part of the top surface of the base. Removable channel cover 44 may be removed and slid, snapped, or placed back into place covering inset channel 42. FIG. 5 is a bottom view of an embodiment of removable channel cover 44. Removable channel cover 44 has two perpendicular slats 66, which engage with the inner surface of circuit board mold 60. FIG. 8 is a sectional of FIG. 6 that shows removable channel cover 44 further secured in place by screws which extend into circuit board mold 60. FIG. 6 also shows perpendicular slats 66 of removable channel cover 44 engaged with the inner surface of circuit board mold 60.

FIG. 6 is a sectional view of FIG. 2. In an embodiment, magnet 64 is positioned inside cover 33 and is attached to base 34 or scanner housing 55. Most preferably, magnet 64 is built into base 34. Base 34 has a cut out specifically for magnet 64 to be placed into such that magnet 64 is flush with the base top surface 36. Magnet 64 is positioned off center and closest to the side of button 62. Magnet 64 has sufficient strength to allow scanner 26 to take a scan only when a user places a scannable object in the focal point of scanner 26.

Figure 9:
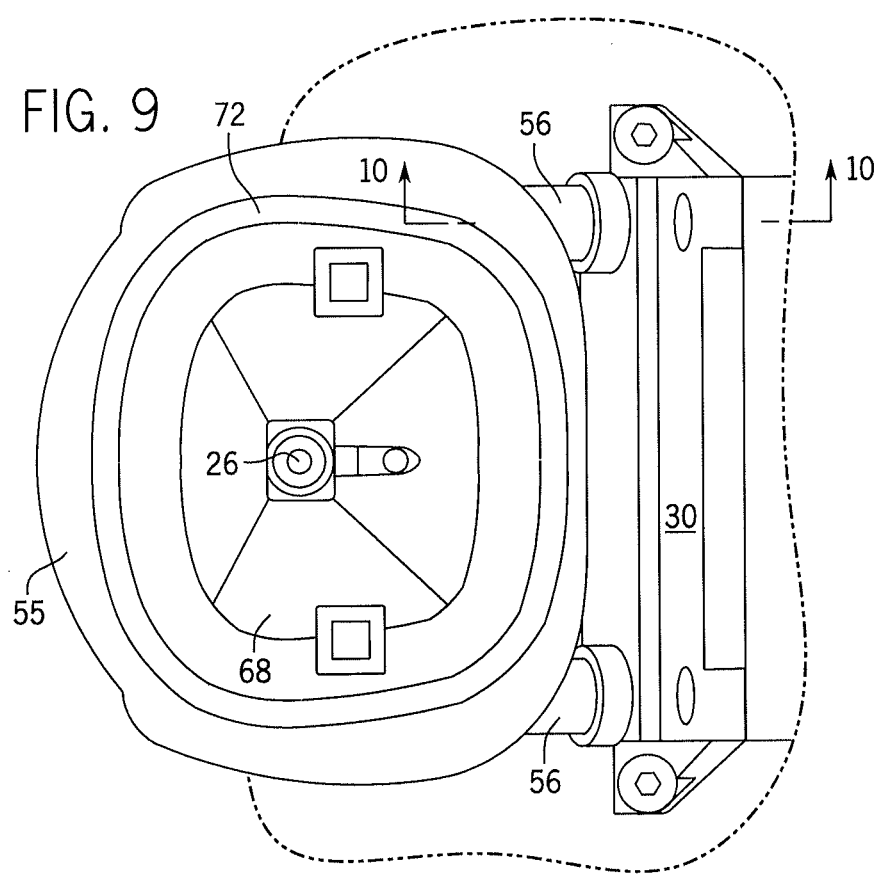
FIG. 9 is a top view of the scanner in FIG. 1.

FIG. 9 is a top view of scanner 26. Scanner 26 has conical walls 68 inside scanner housing 55. Scanner housing 55 includes shield 70, which extends beyond conical walls 68. Preferably, shield 70 comprises shield wings 72, which extend further on two opposite sides (see FIG. 4).

In an embodiment, scanner 26 is capable of reading identifiers such as conventional barcodes, etched matrixes, or any other optical indicator on an implant. In an embodiment, scanner 26 is equivalent to the scanner in Motorola Symbol DS6707-DP. In an embodiment, the reader further comprises a light emitting diode (LED) 28 for enhancing the visual indication of scanner 26, as shown in FIGS. 2B and 3B.

In an embodiment, reader 20 comprises an optional transparent sterile sheath 22 as shown in FIGS. 3A and 3B which encases cover 33 of reader 20. Transparent sterile sheath 22 can be partially or completely transparent, while in at least some embodiments, transparent sterile sheath 22 can be provided without transparent portions, provided that scanner 126 includes the capability to scan identifiers through the level of transparency provided by transparent sterile sheath 22. In at least some embodiments, sterile sheath 22 can be at least partially opaque, with the exception of at least a portion that covers aperture 54. Transparent sterile sheath 22 has sheath top surface 75 and sheath side wall 76. Preferably, sheath top surface 75 is slightly convex to deflect ambient light. In at least some embodiments, the convex portion of sheath top surface 75 can be substantially limited to the portion covering aperture 54. The degree of convexity is such that the transparent sheath reflects ambient light that interferes with the reader. Ambient light is background light typically present in an operating room. In an embodiment, sheath side wall 76 has at least one radial pin slot 77 designed to receive radial pin 52 of cover 33. FIG. 3A shows an embodiment in which two radial pin slots 77 are in an inverted "L" shape, such that when radial pin 52 of cover 33 engages with the radial pin slots 77 and the transparent sterile sheath 22 is twisted, it temporarily locks the transparent sterile sheath 22 in place by hindering vertical movement. One skilled in the art would understand the transparent sterile sheath could be temporarily locked into place over cover 33 in various manners. Alternatively, transparent sterile sheath 22 may just rest over cover 33 without any mechanism to lock the sheath in place.

Transparent sterile sheath 22 is designed such that when transparent sterile sheath 22 is engaged with housing structure 32 the area of sheath top surface 75 directly above aperture 54 of housing structure 32 is at the focal point of scanner 26. Placement of an implant with an indicator directly on the sheath top surface 75 directly above aperture 54 allows for the scanner to read the indicator without an operator having to hover the implant device over aperture 54 and search for the focal point of the scanner 26.

In an embodiment, transparent sterile sheath 22 is formed of a single piece of rigid transparent plastic. In an embodiment, transparent sterile sheath 22 is formed of a non-conductive, flexible, easily distortable, resilient material, which can be sterilized. Preferably, transparent sterile sheath 22 is disposable, such that transparent sterile sheath 22 is disposed of after identifiers have been received for all the medical implants implanted in a single patient during an operation.

The thickness of transparent sterile sheath 22 is such that does not interfere with the reader device's ability to obtain data from an identifier on a medical implant. Transparent sterile sheath 22 may be made of one or more of an elastomer, plastic, rubber, polyethylene, or polypropylene, among other materials that result in a functioning transparent sterile sheath 22 of the invention. In an embodiment, transparent sterile sheath 22 is made of a rigid, transparent plastic such as polycarbonate.

Transparent sterile sheath 22 may have additional properties that enhance the reader device's abilities. For example, in an embodiment, the sheath top surface 75 has magnifying abilities to allow a reader device to gather information from a smaller identifier such as a barcode or a 2D-grid or matrix the size of 2 millimeters (mm) by 2 mm, and even 1.4 mm by 1.4 mm. In an embodiment, the transparent sterile sheath 22 adheres to reader 20 such that the seal between transparent sterile sheath 22 and cover top surface 46 creates a vacuum between transparent sterile sheath 22 and the reader device. A vacuum between reader 20 and transparent sterile sheath 22 allows for improved reading of reader 20.

Assembly 10 comprising table top reader 20 further increases the efficiency of implant tracking by allowing a user to place the implant having the identifier on the surface of a transparent sheath for an accurate, automatic scan of the identifier. The user is not having to spend precious time waving/hovering the implant in front of a handheld reader to find the focal point of the scanner to obtain a scan during surgery. The inventive structure of reader 20 provides an efficient and sterile implant tracking device.

Handheld Reader

Figure 11:
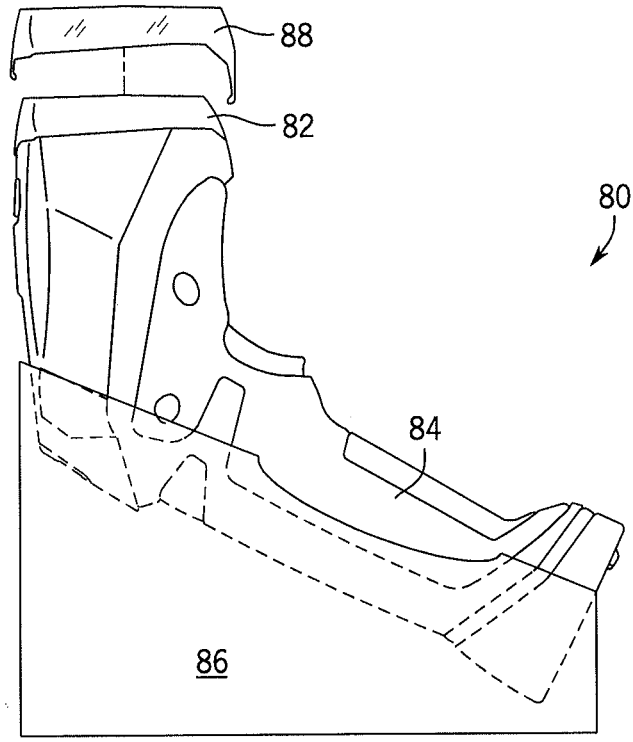
FIG. 11 is a schematic of a handheld reader and cradle of an embodiment of the invention.

FIGS. 11-14 are embodiments of an assembly comprising handheld reader 80 including reader lens 82 and handle 84. Handheld reader 80 contains an optical scanner. In an embodiment, the optical scanner is equivalent to that found in Motorola Symbol DS6707-DP. FIG. 11 is an embodiment of an assembly comprising a handheld reader 80 positioned in cradle 86, wherein handheld reader 80 is detachably connected to the cradle. Handheld reader 80 further comprises transparent sterile lens cover 88 which allows for an implant bearing an identifier to come into close proximity to the lens cover 88 for scanning without compromising the implant's sterility. Transparent sterile lens cover 88 may have magnifying abilities to allow the reader device to gather information from a smaller barcode or a 2D-grid or matrix the size of 2 millimeters (mm) by 2 mm, and even 1.4 mm by 1.4 mm. The focal point of the scanner is just above (1-2 mm) the surface of transparent sterile lens cover 88.

Figure 12:
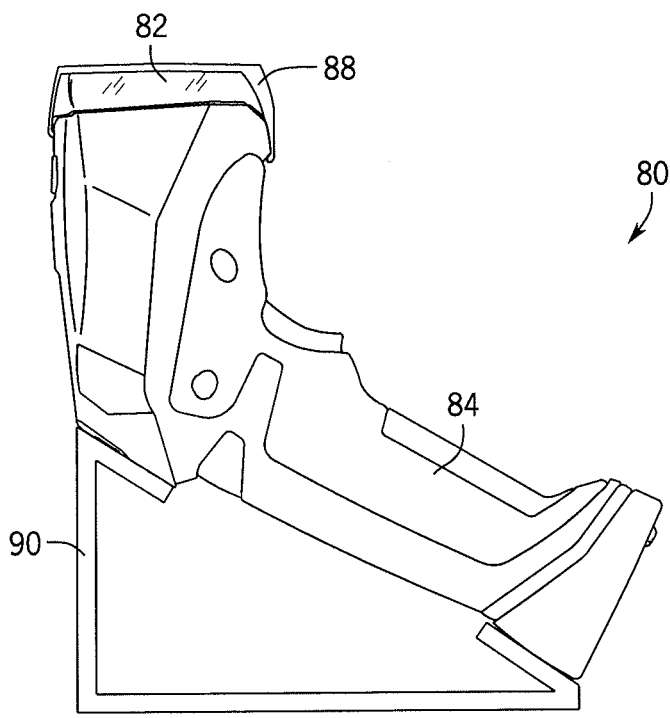
FIG. 12 is a schematic of the handheld reader and a base structure.

FIG. 12 shows an embodiment of handheld reader 80 further comprising base structure 90 built off of handle 84 of the handheld reader that allows the user to place handheld reader 80 on a flat surface and operate handheld reader 80 without holding onto it. FIG. 12 shows transparent sterile lens cover 88 engaged with reader lens 82. In an embodiment, transparent sterile lens cover 88 releasably attaches to reader lens 82 to temporarily fix transparent sterile lens cover 88 in place over reader lens 82 of handheld reader 80. In an embodiment, transparent sterile lens cover 88 snaps into place over reader lens 82 with the application of minor force.

Table Top-Handheld Reader

Figure 14:
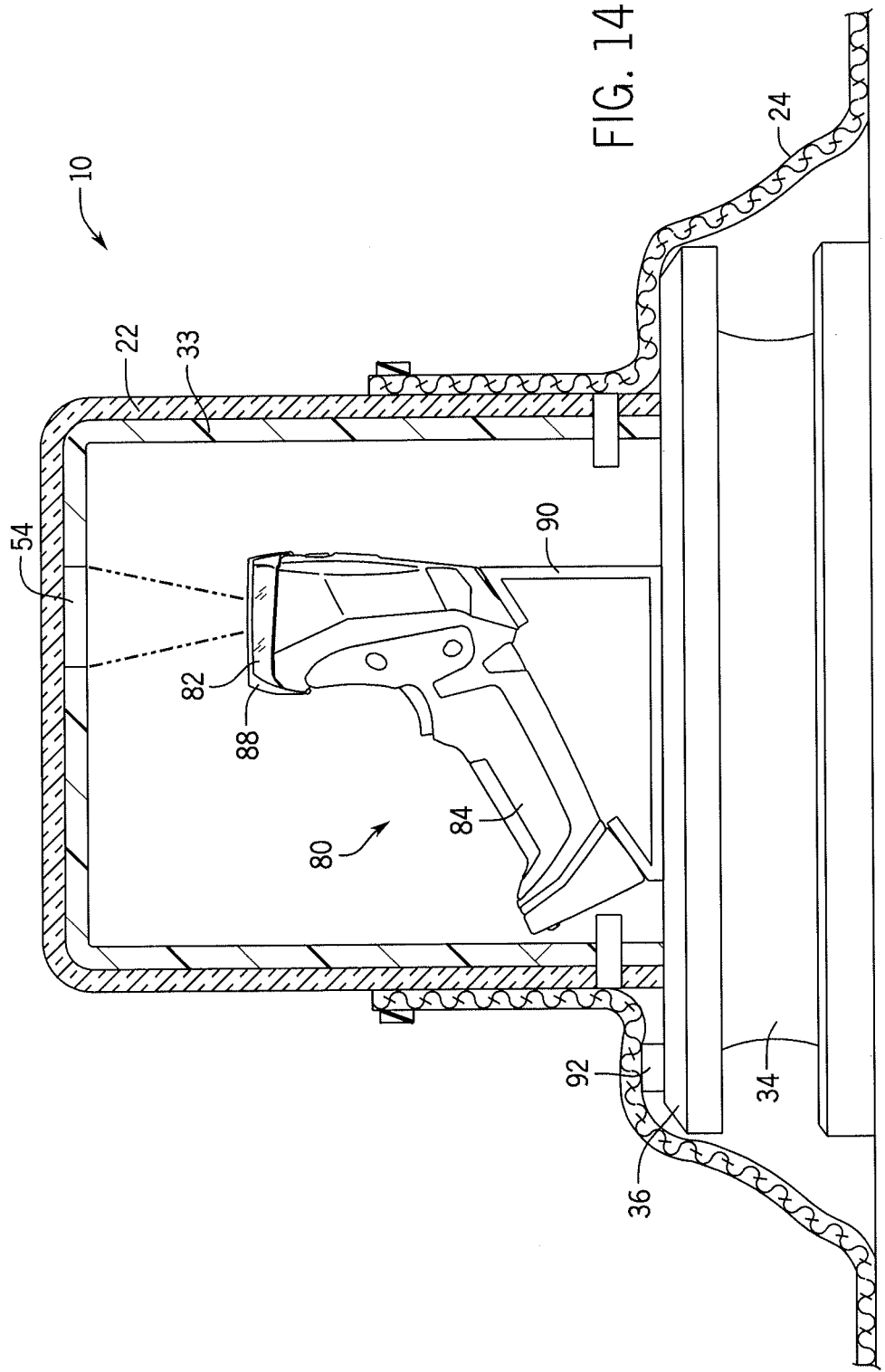
FIG. 14 is a schematic of the reader of FIG. 12 enclosed within the housing structure of the assembly of FIG. 1.

In an embodiment shown in FIG. 14, handheld reader 80 is placed inside housing structure 32 of FIG. 1 by replacing scanner 26 and scanner mounting structure 30. Handheld reader 80 may be positioned in cradle 86 which is secured and/or mounted to base 34. In an embodiment, handheld reader 80 does not contain handle 84. Alternatively, handheld reader 80 may comprise base structure 90 which is mounted to base 34. Reader lens 82 is positioned below aperture 54 which is covered by transparent sterile sheath 22 such that the focal point of handheld reader 80 is on or right above the surface of transparent sterile sheath 22 in the area above aperture 54. As a typical handheld reader is operated by a trigger on handle 84, a scanner switch 92 may be positioned on base 34 outside of cover 33 which allows the user to press to activate handheld reader 80. Alternatively, magnet 64 may be positioned near handheld reader 80 to keep handheld reader 80 activated and continually taking scans when an implant having an identifier is placed on the focal point. The handheld reader 80 may or may not include transparent sterile lens cover 88. Any of the transparent sterile sheath 22, transparent sterile lens cover 88 and reader lens 82 may have magnifying abilities that are compatible with each other.

Medical Drape

Assembly 10 further comprises a medical drape. Medical drape 24 may be made of conventional medical drape material. Alternatively, medical drape 24 is transparent and flexible to enable use of a control panel on a reader device. Medical drape 24 may allow for the manipulation of buttons, calibrating dials, and adjusting knobs frequently associated with reader 20.

As shown in FIGS. 1, 2A, and 2B, medical drape 24 temporarily attaches to side wall 76 of transparent sterile sheath 22 and extends out radially to maintain a sterile environment. Medical drape 24 may comprise an elastic band to attach to sheath side wall 76. Alternatively, medical drape 24 may clip onto sheath side wall 76 for attachment. Any attachment mechanism may be used to attach medical drape 24 to sheath side wall 76. In at least some embodiments, medical drape 24 can be permanently adhered to sheath side wall 76 prior to installation on reader 20.

Figures 13A, 13B:
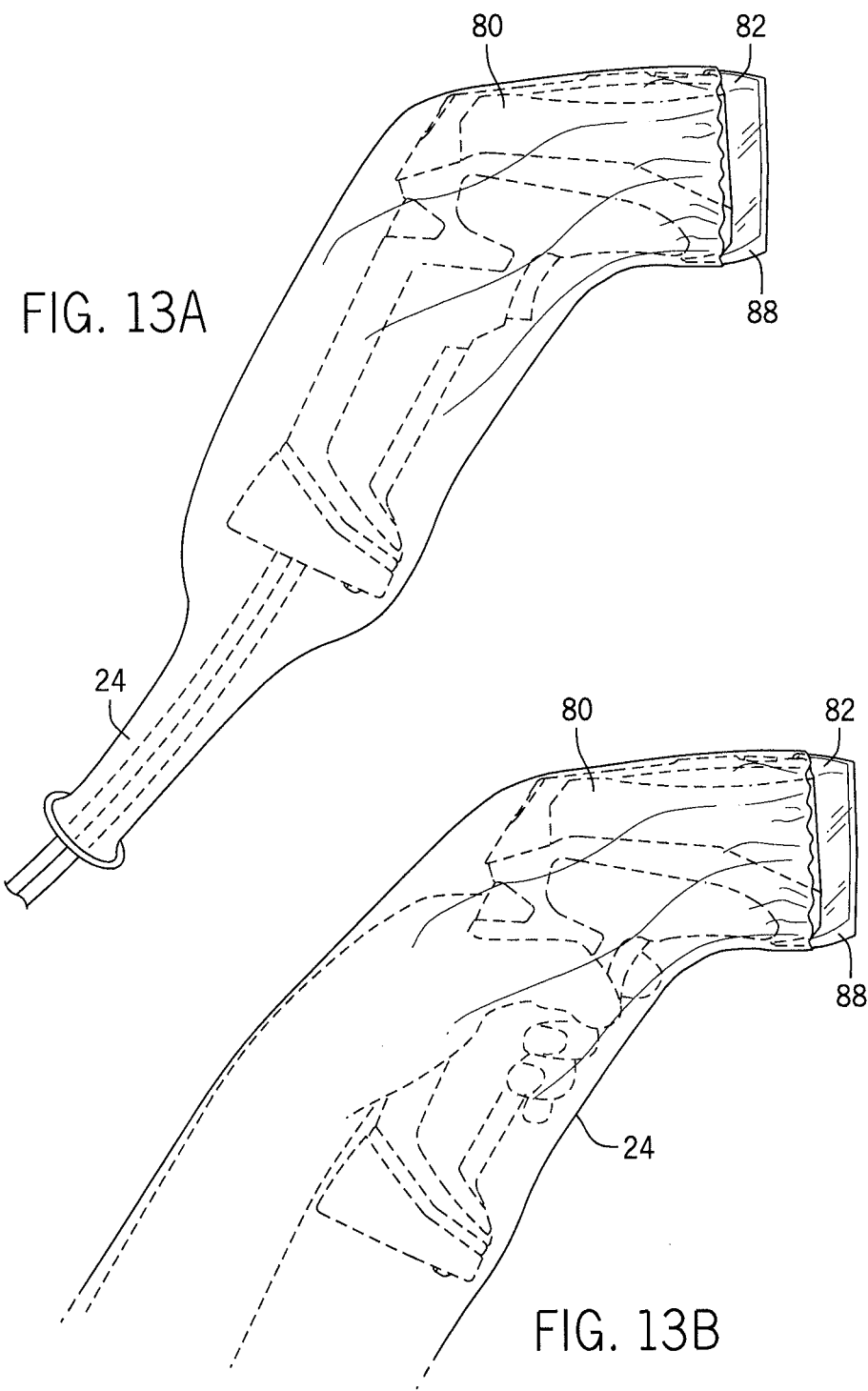
FIG. 13A is a schematic of the handheld reader enclosed within a medical drape.
FIG. 13B is a schematic of the handheld reader and hand of a user enclosed within a medical drape.

FIGS. 13A and 13B show an embodiment in which medical drape 24 is attached to transparent sterile lens cover 88 of handheld reader 80. Medical drape 24 unrolls from lens cover 88 and creates a barrier between the reader device and the sterile environment. In the situation depicted in FIG. 13A, the user, usually wearing a sterile glove, would generally operate handheld reader 80 by holding reader 80 on top of medical drape 24. Alternatively, as shown in FIG. 13B, the medical drape is designed to fit over the user's hand.

Medical drape 24 may be made of conventional medical drape material, although various other materials can be utilized alone or in combination. Alternatively, medical drape 24 is transparent and flexible to enable use of a control panel on a reader device. Medical drape 24 may allow for the manipulation of buttons, calibrating dials, and adjusting knobs frequently associated with reader 80.

Computer

Assembly 10 comprises computer 25 in communication with reader 20. Computer 25 is equipped with software that allows recording and manipulation of input data from reader 20. The software is designed to receive information (manufacturer's information, lot number, serial number, etc.) obtained from the identifier upon being scanned by the reader. The software further allows the user of the computer to input data that indicates where the screw was implanted according to the surgeon's instruction. The location data of where the implant is placed in the patient may be aided by the software, which pulls up an anatomical image where the user of the computer can then just select visually where the implant was inserted. Computer 25 is usually outside the sterile field. Alternatively, the computer may be part of the same assembly as the reader. The term computer is meant to encompass desktop computers, laptops, tablets, and pads, among others, as well as various other devices capable of receiving and storing data.

Additional Components

Assembly 10 may further include additional components such as a keyboard, mouse, stylus, printer, display screen or other interface that allows a user to interact with the system such as to input information, issue commands, power the device on and off, perform file management, upgrade software and database information, monitor output, receive feedback and perform other administrative and non-administrative tasks.

Implant Tracking Method

The present disclosure provides a method of tracking a medical implant including providing a reader as described above, placing a transparent sterile sheath over the housing structure of the reader device, placing an implant device having an identifier on the top surface of the transparent sterile sheath above the aperture of the housing structure, and scanning the identifier of the implant device to record the stored data.

An advantage of the present disclosure is a method of tracking an implant that allows for greater efficiency and ease of use by the operator, while maintaining a sterile environment. By using the implant tracking method of the present disclosure, the user does not have to hand record the implant identifying information, which allows a faster operating procedure. Nor does the user need to spend time finding the focal point of the scanner to obtain an accurate read of the identifier. The method of the present disclosure is designed to allow a user to place the implant with the identifier onto its top surface to obtain an accurate scan of the identifier and then quickly pass the implant to the surgeon for implantation, all while not compromising the sterility of the implant or surgical field. The scanner takes a scan automatically when the identifier is placed on the top surface of the transparent sheath above the aperture. Thus, the user does not have to bother with a button to activate the scanner to take a scan while handling in the implant.

In an embodiment, the identifier is a conventional 4×4 millimeter (mm) matrix, or a non-conventional 2×2 mm, or 1.4×1.4 mm matrix laser etched directly onto the implant device. By having the identifier etched directly into the surface of the medical implant, the user does not have to bother with scanning external tags to the medical device and removing the tag prior to the implant procedure, thus allowing for a more efficient method of tracking.

The method further includes positioning a medical drape to cover the remaining portions of a reader device. In an embodiment, the positioning of the medical drape to cover the remaining portions of a reader device includes unrolling the medical drape from the transparent lens cover to extend around the remaining portions of the reader device. In an embodiment, the positioning of the medical drape to cover the remaining portions of a reader device further includes unrolling the medical drape to extend around the remaining portions of the reader as well as the user's arm operating the reader device.

Referring to FIGS. 15-19, an exemplary embodiment of implant tracking assembly 110 is provided that includes various components that are similar in form and/or function to various components described above with respect to implant tracking assembly 10. It shall be understood that various components described below, with like names to those described above, can include one or more of the aforementioned features, such as shapes, dimensions, materials, configuration, uses, etc., as described above.

Figure 15:
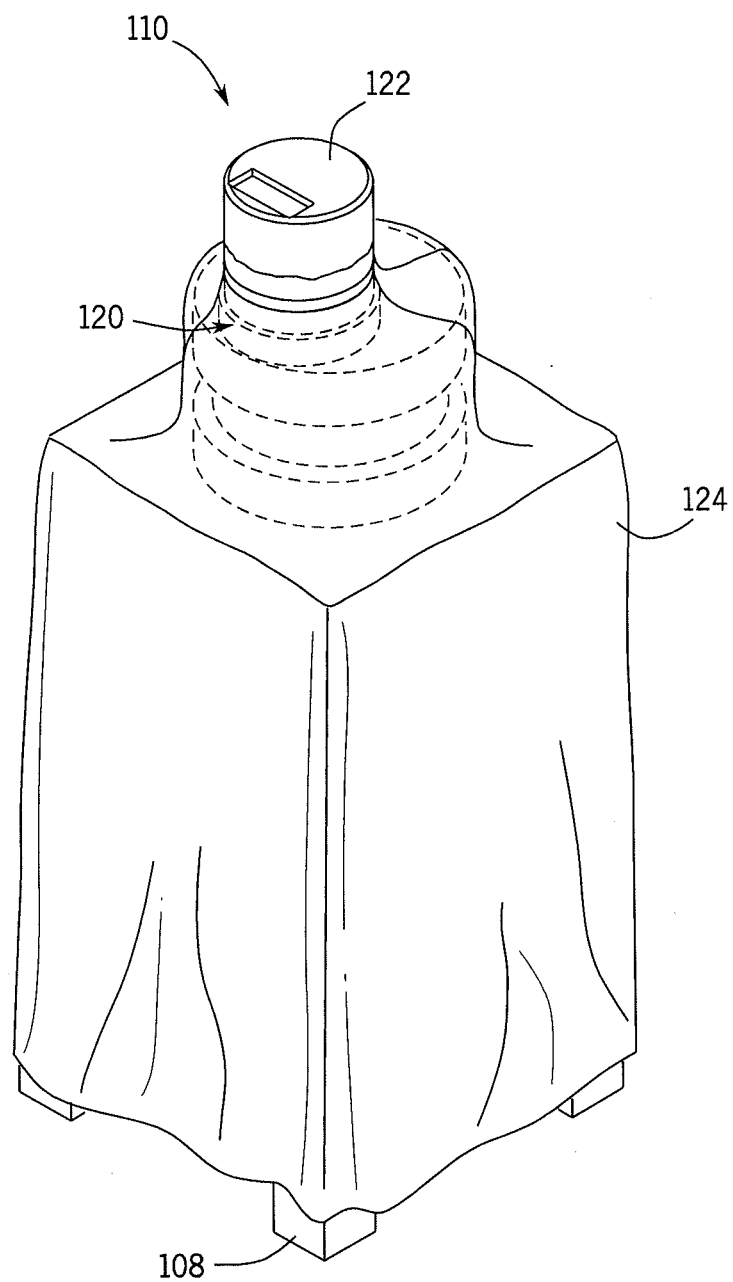
FIG. 15 is a schematic of another embodiment of the implant tracking assembly that includes a reader, a sheath, and a medical drape.
Figure 16:
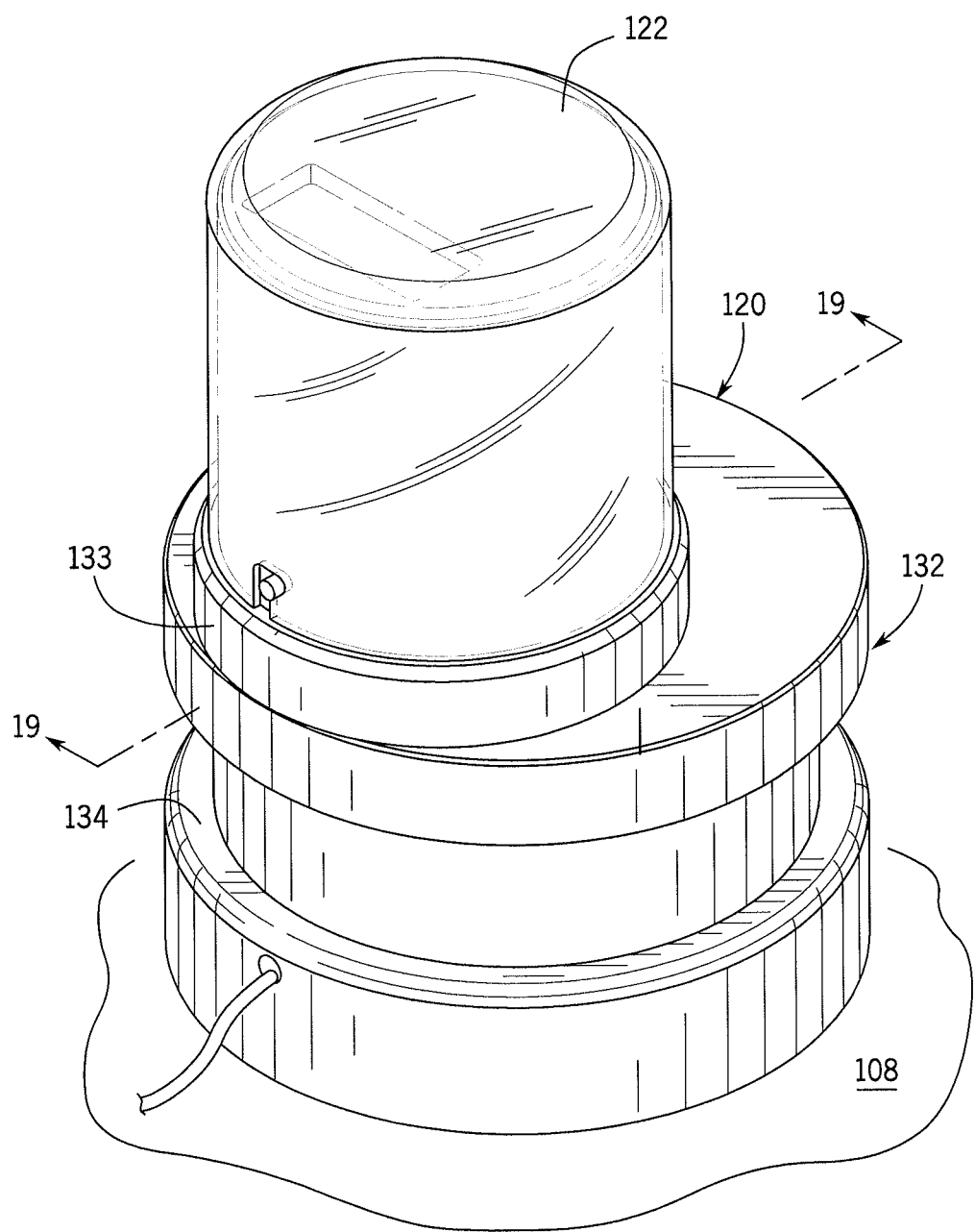
FIG. 16 is a perspective view of the reader and sheath of FIG. 15.
Figure 17:
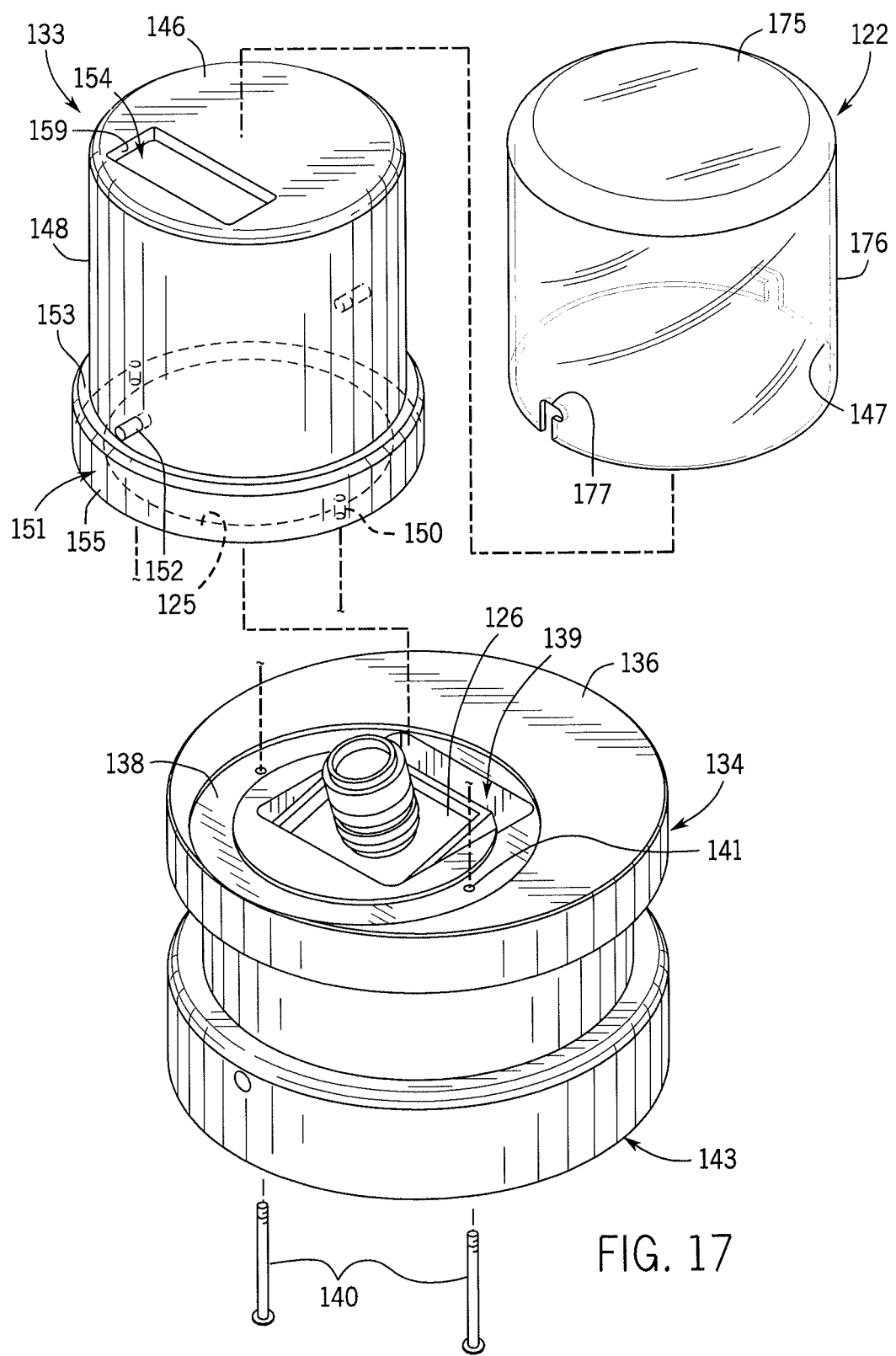
FIG. 17 is an exploded perspective view of FIG. 16.

FIG. 15 provides a perspective view of implant tracking assembly 110 with reader 120, transparent sterile sheath 122, and medical drape 124. FIG. 16 provides a perspective view of reader 120 and transparent sterile sheath 122. Reader 120 includes housing structure 132 having cover 133 and base 134. Referring to FIG. 17, an exploded perspective view of reader 120 and transparent sterile sheath 122 is provided. Base 134 includes base top surface 136 having inset groove 138 formed therein. Inset groove 138 is sized and shaped to fittingly receive planar cover bottom surface 135 of cover 133. Base pin holes 141 are provided, which pass through inset groove 138 to allow vertical pins 140 to pass therethrough and secure to pin holes 150 in cover 133. In this regard, cover 133 can be secured to base 134 without the need for protruding fasteners. In addition, base 134 includes cavity 139, which extends from base top surface 136 towards base bottom 143. Cavity 139 is configured to receive scanner 126, such that at least a portion of scanner 126 is recessed below base top surface 136. In at least some embodiments, cavity 139 forms a rectangular shape sized to accommodate scanner 126, while in other embodiments, cavity 139 is sized and shaped to accommodate various other types, sizes, and shapes of scanners.

As seen in FIG. 17, transparent sterile sheath 122 includes generally circular sheath top surface 175 and cylindrical sheath side wall 176 that extends perpendicularly downward from sheath top surface 175 to sheath bottom surface 147. As discussed above, in at least some embodiments, sheath top surface 75 is slightly convex to deflect ambient light. In addition, transparent sterile sheath 122 includes one or more radial pin slots 177, which are configured to engage one or more radial pins 152 on cover 133 to provide securement of transparent sterile sheath 122 to reader 120. Transparent sterile sheath 122 is sized and shaped to fit over cover 133. More particularly, cover 133 includes generally circular cover top surface 146 and cylindrical side wall 148 that extends substantially perpendicularly downward from cover top surface 146 to flange 151. Flange 151 includes a flange top surface 153, which is configured to receive sheath bottom surface 147 when transparent sterile sheath 122 is installed. Flange side wall 181 extends downward towards base 134 and includes cover bottom surface 135, which is configured to rest on the inset groove 138 when cover 133 is installed on base 134. Although transparent sterile sheath 122 is intended to fit over cover 133, one or both of transparent sterile sheath 122 and cover 133 can vary in shape to provide greater or fewer conforming surfaces.

Cover 133 further includes aperture 154 having an aperture perimeter 159, where aperture 154 allows scanner 126 to obtain information from exemplary object 161 (see FIG. 19) when positioned over the aperture 154. Aperture 154 may be positioned in one of various locations about the cover 133 to provide suitable access to a user and to accommodate the field of view of the scanner 126. In addition, if scanner 126 is configured to sense identifier 111 having a non-optical component (e.g., RFID), then the aperture 154 may be omitted entirely and the cover 133 comprised of a material that allows signal-based communication therethrough, or the cover 133 may include a portion of the cover material that is capable of allowing signal-based communication therethrough.

Figure 18:
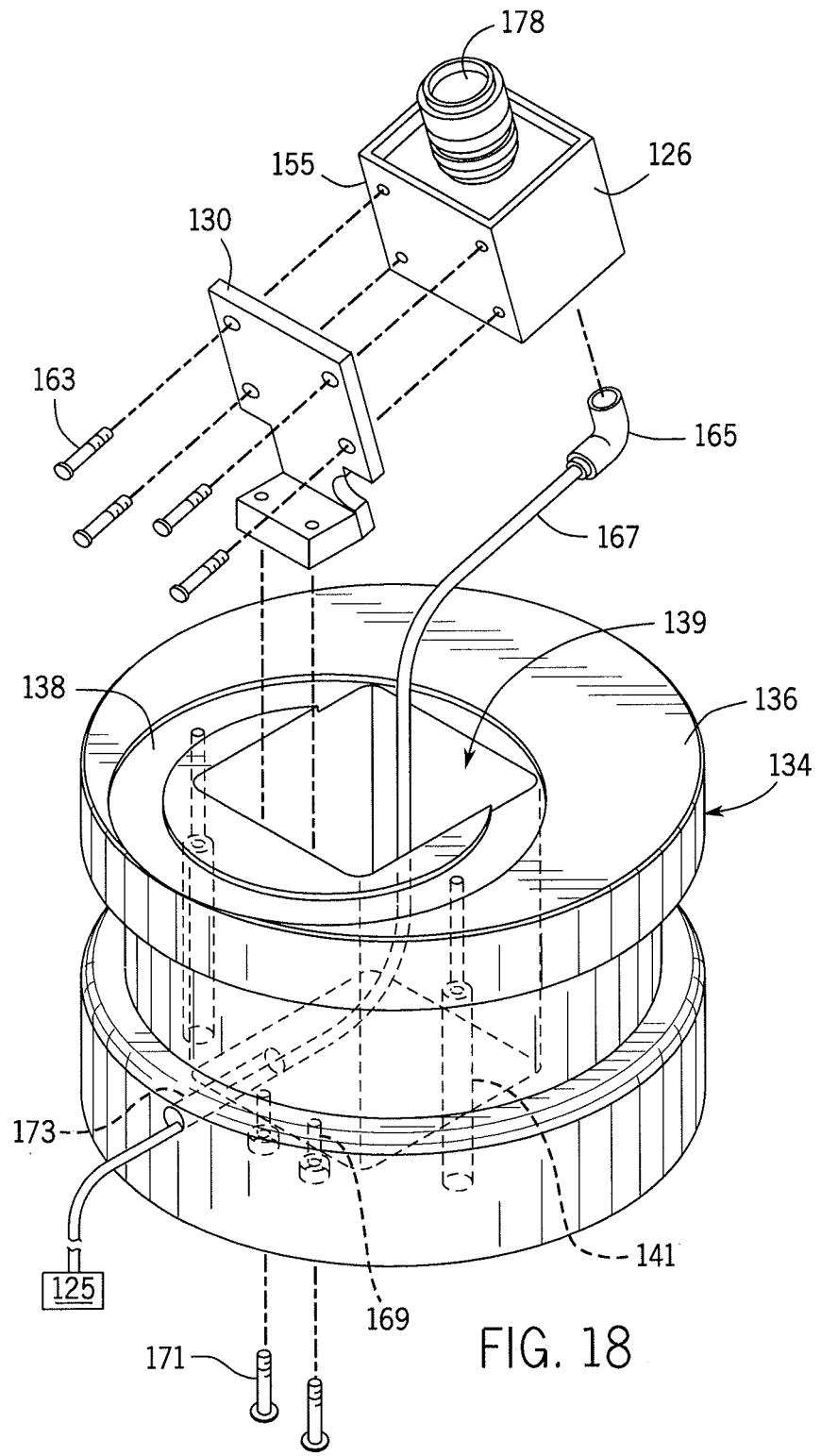
FIG. 18 is an exploded perspective view of various portions of the reader of FIG. 15.

Referring to FIG. 18, an exploded perspective view of reader 120 with cover 133 removed is provided. As shown, scanner 126 includes scanner housing 155 that is secured to scanner mounting structure 130 by one or more scanner fasteners 163. Scanner mounting structure 130 is shaped to provide a suitable angle for scanner 126 to read identifiers 111 through aperture 154. Scanner 126 is connected to plug 165 at one end of cord 167. Plug 165 provides a removable connection between cord 167 and scanner 126. Cord 167 connects scanner 126 to another device, such as computer 125, as discussed above. Base 134 includes mount passages 169 configured to receive mount fasteners 171 that are inserted through mount passages 169 and secured to scanner mounting structure 130. In this manner, scanner 126 can be installed in reader 120 by securing scanner 126 to scanner mounting structure 130, plugging in plug 165, and inserting both into cavity 139 and securing to base 134. Base 134 further includes cord passage 173 that extends from cavity 139 to outside base 134 to provide an outlet for cord 167.

Figure 19:
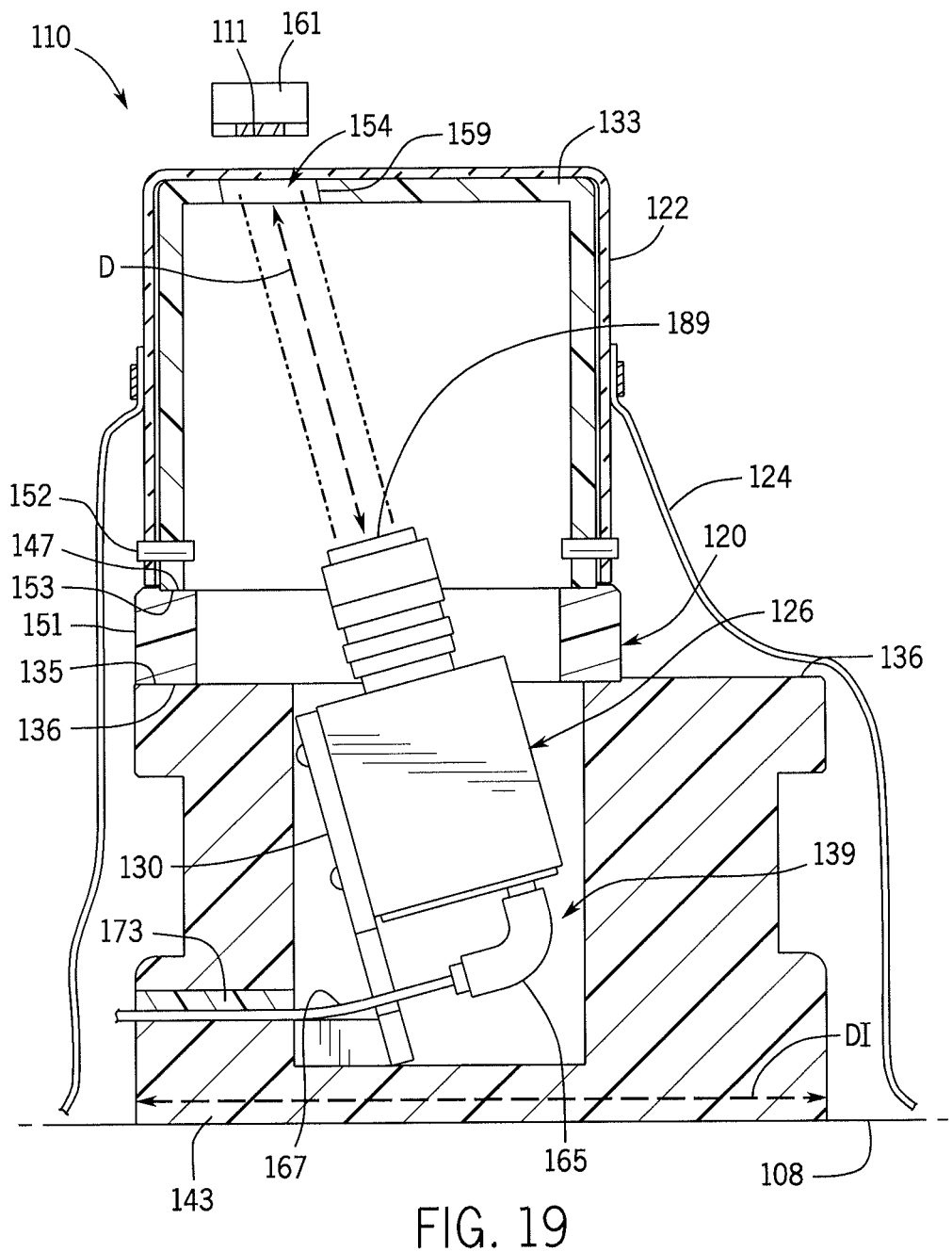
FIG. 19 is a sectional side view taken at line 19-19 of FIG. 16.

Referring to FIG. 19, a sectional side view taken at line 19-19 of FIG. 16 is provided. For illustrative purposes, although medical drape 124 was not shown in FIG. 16, it has been included on FIG. 19. As shown in FIG. 19, scanner 126 includes lens assembly 178 extending from scanner housing 155 and directed towards aperture 154. Lens assembly 178 includes front surface 189, where front surface 189 extends to aperture 154 along a distance D, where distance D is between about 3 inches to about 5 inches. In at least some embodiments, scanner 126 is a Model No. DataMan 500 barcode reader, as manufactured by COGNEX located in Natick, Mass. However, in at least some other embodiments, other models, types, and brands of scanners can be provided. The DataMan 500 model, as well as other types of scanners can be modified from their original manufactured form. For example, the original scanner housing can be reduced in size to fit accordingly in cavity 139, such as by removing portions of the scanner housing without damaging or otherwise rendering other necessary portions or components non-functional. Scanner 126 is configured to read identifier 111, which is located on object 161, such as a medical implant, as discussed above. Identifier 111 is communicated to computer 125 for recordation and/or display. It shall be understood that various components described below with like names to those described above, can include similar functions and features, such as shapes, dimensions, materials, configuration, uses, etc., as described above.

Figure 20:
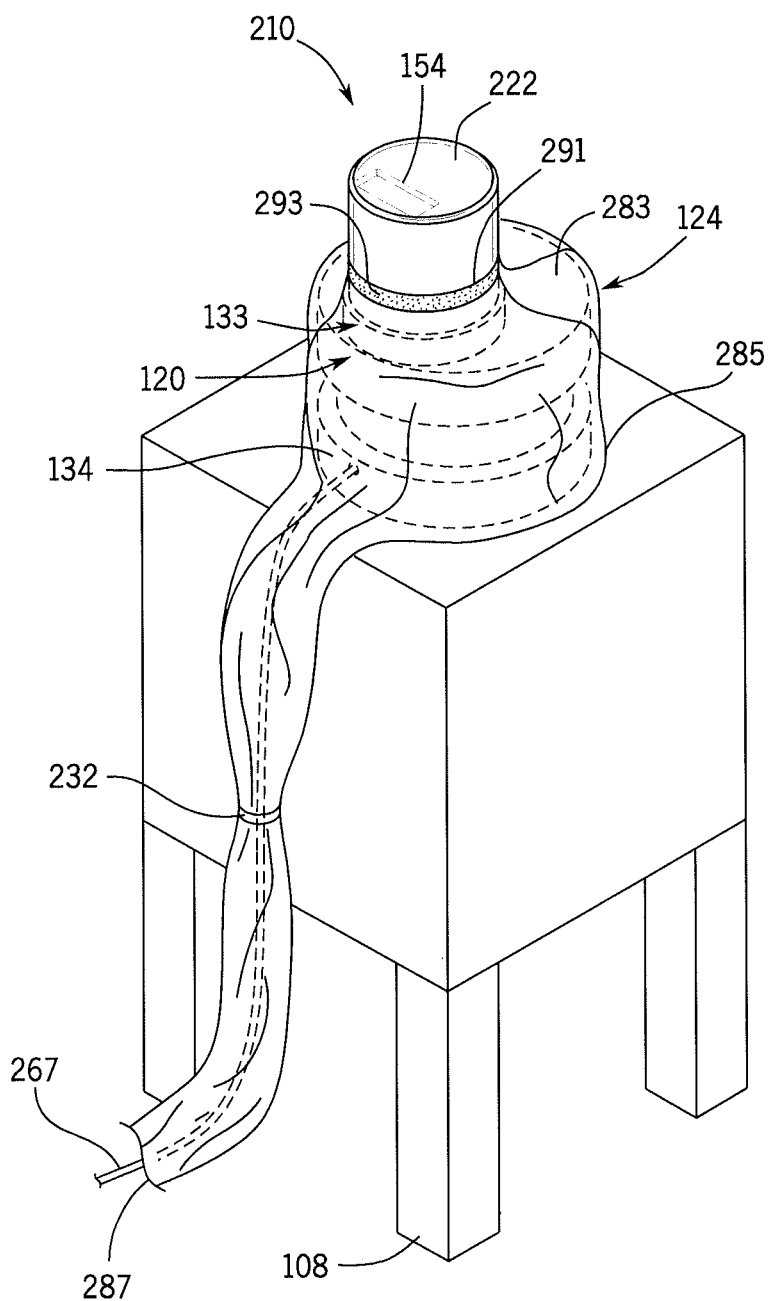
FIG. 20 is a schematic of an embodiment of the implant tracking assembly.

Referring to FIG. 20, implant tracking assembly 210 is illustrated, which includes reader 120 enclosed by sheath 222 and drape 224. As shown, implant tracking assembly 210 is positioned on table 108, which is representative of one of many types of support surfaces that implant tracking assembly 210 can be situated on during a medical procedure. Additionally, in at least some embodiments, sheath 222 is similar or identical to transparent sterile sheath 22 and transparent sterile sheath 122. As shown, drape 224 extends from sheath 222, over reader 120, and over one or more cords 267 connected to reader 120. Drape 224 is secured to sheath 222 in one of a temporary or permanent manner, as discussed further below.

Figure 21:
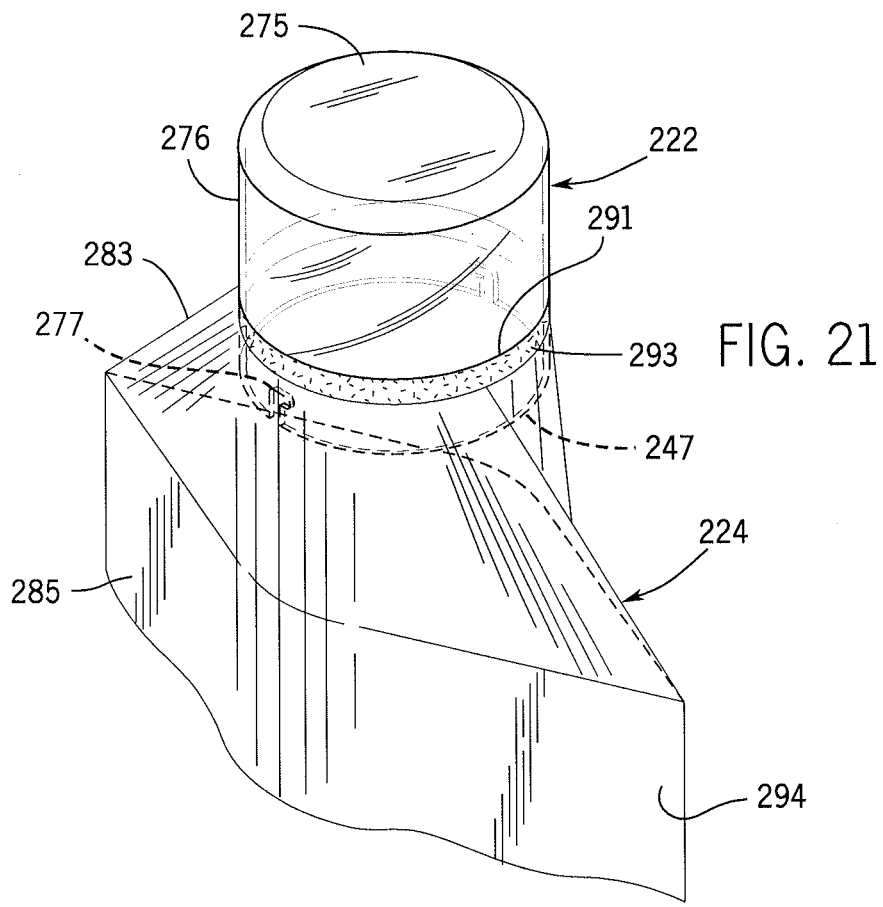
FIG. 21 is a perspective view of an embodiment of the sheath and drape of FIG. 20.
Figure 22:
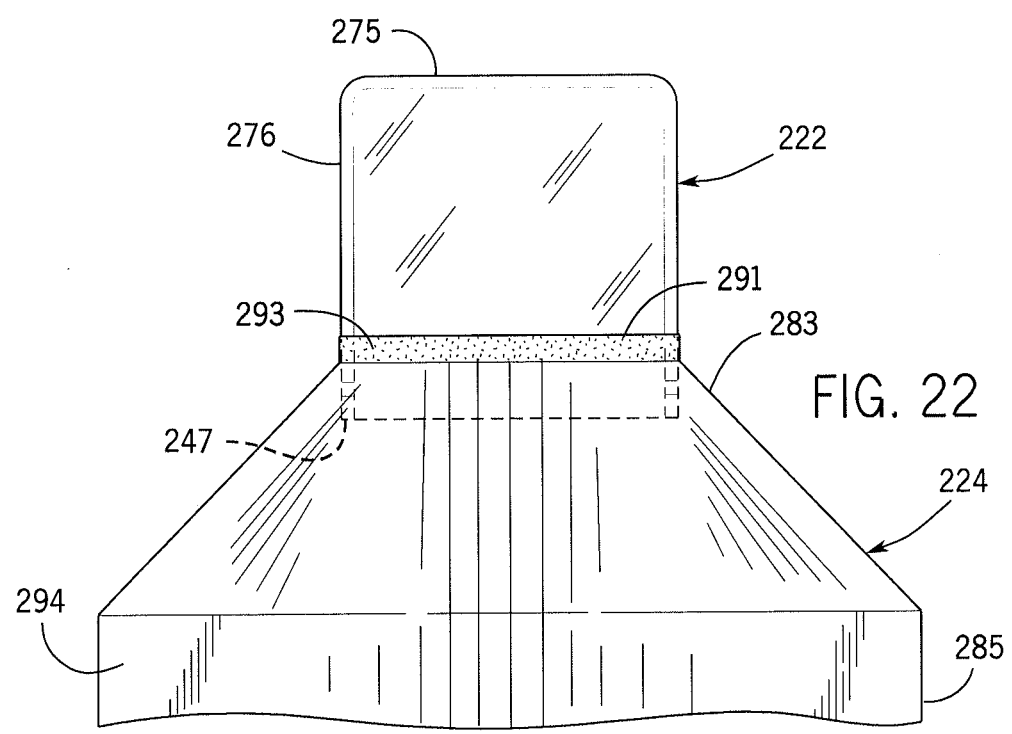
FIG. 22 is a side view of the sheath and drape of FIG. 21.

Referring to FIGS. 21 and 22, a perspective and side view of sheath 222 and drape 224 are illustrated. As shown, sheath 222 includes generally circular sheath top surface 275 and cylindrical sheath side wall 276 that extends perpendicularly downward from sheath top surface 275 to sheath bottom surface 247. In at least some embodiments, sheath top surface 275 may be slightly convex to deflect ambient light. In at least some embodiments, sheath 222 includes an interlocking engagement, such as one or more radial pin slots 277, which are configured to engage one or more radial pins 152 on cover 133 to provide securement of sheath 222 to reader 120. In other embodiments, sheath 222 may be positioned over cover 133 without an interlocking engagement.

The sheath 222 is sized and shaped to fit over cover 133, as such, although sheath 222 is illustrated as cylindrical, other shapes, such as rectangular, pyramidal, etc. may be utilized sheath 222 to accommodate various cover 133 shapes. Similar to transparent sterile sheaths 22 and 122, sheath 222 may be transparent, partially transparent or include varied levels of transparency. In addition, sheath 222 can vary in signal-based transparency as well as optical transparency, wherein signal-based transparency allows for transmission of a non-optical scanning signal (not optically dependent) between reader 120 and identifier 111 (FIG. 19) of an object 161, and therefore, may be independent of the level of optical transparency or sheath coloring.

As discussed above, cover 133 includes aperture 154 having an aperture perimeter 159, wherein aperture 154 allows scanner 126 to obtain information from object 161 (see FIG. 19) when positioned over aperture 154. As sheath 222 covers cover 133, the scan will also pass through sheath 222. To accommodate scanning therethrough, sheath 222 is comprised of a material that is completely or at least partially optically transparent or signal-based transparent. For example, sheath 222 may be substantially opaque, but include a window (not shown) that is positionable over at least aperture 154 to allow scanner 126 to view or otherwise communicated with identifier 111 of object 161.

Referring to FIGS. 21 and 22, sheath 222 is shown with drape 224. The drape 224 includes drape upper portion 283 and drape lower portion 285, where the drape upper portion 283 includes a first end 291 of drape 224 and drape lower portion 285 includes a second end 287 of the drape 224. The drape 224 is secured to and extends radially from sheath side wall 276 to enclose reader 120, and various related components, such as electrical cords and control panels, among other things.

As shown, first end 291 of drape 224 is secured to sheath side wall 276 along securement band 293, which encircles sheath side wall 276. The securement can be one of temporary or permanent and in at least some embodiments, provides an airtight seal. In a temporary configuration, drape 224 may be held to sheath 222 by a fastener, such as a rubber band or clip. Any attachment mechanism may be used to attach drape 224 to sheath side wall 276, although in the present embodiment, first end 291 is permanently secured to sheath 222. A permanent securement may be performed in one of various manners, such as heat welding, heat sealing, chemical adhesives, etc. Drape 224 may be comprised of conventional medical drape material or another suitable material, such as vinyl, that is sterilizable and able to provide a sufficient sterile barrier to limit or prevent contamination between reader 120 and the surrounding environment. Drape 224 may be configured with one or more of various levels of transparency, and may be flexible enough to enable use of a control panel on reader 120. More particularly, drape 224 may include sufficient flexibility to allow for the manipulation of buttons, calibrating dials, and adjusting knobs that may be associated with reader 120.

Figure 23:
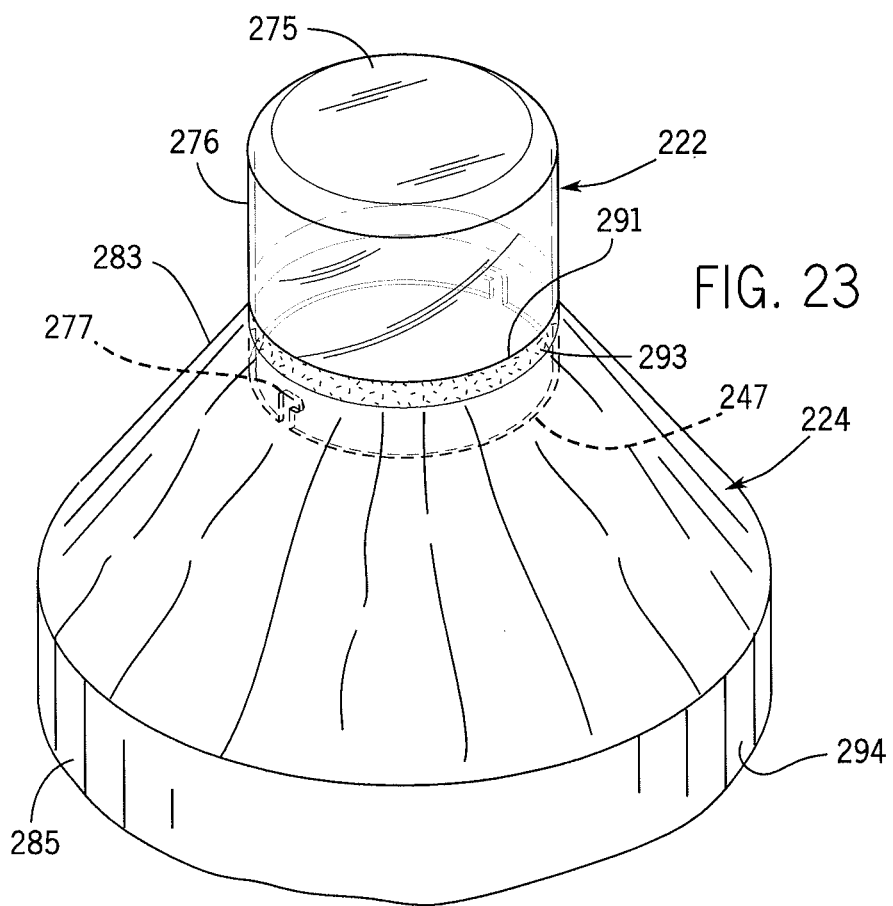
FIG. 23 is a perspective view of another embodiment of the sheath and drape of FIG. 20.
Figure 24:
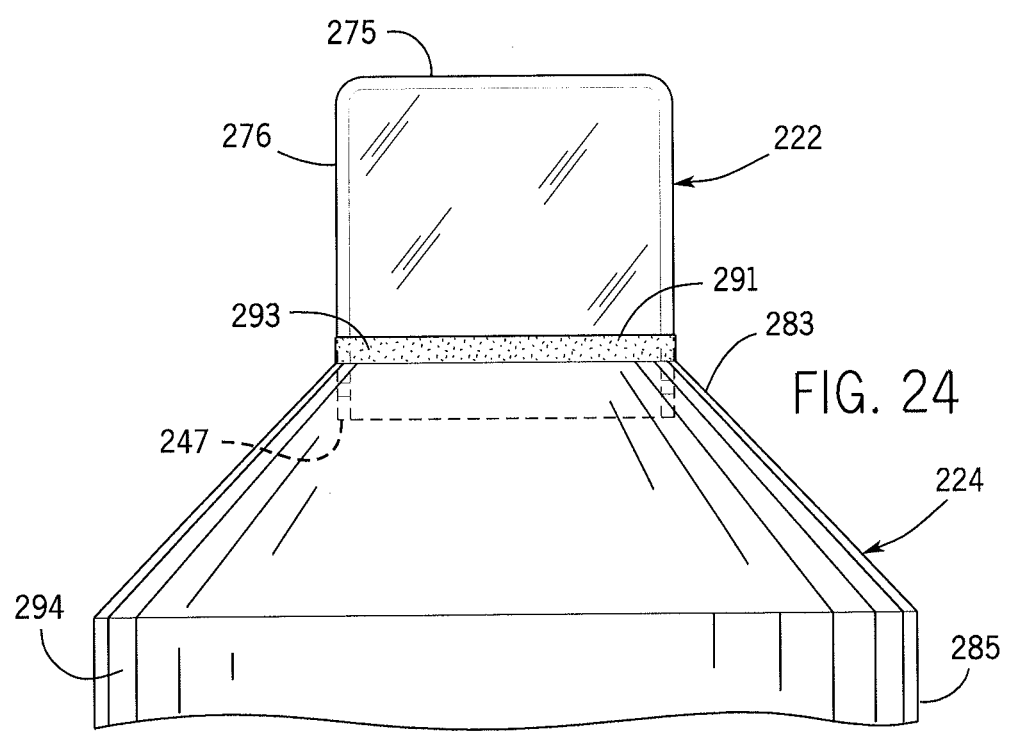
FIG. 24 is a side view of the sheath and drape of FIG. 23.

FIGS. 21 and 22 provide an embodiment of drape 224 that includes a generally pyramidal-shaped drape upper portion 283, which extends from sheath side wall 276 to the drape lower portion 285. The drape lower portion 285 then extends in a linear manner (i.e., parallel sidewalls) along drape sides 294. FIGS. 23 and 24 provide an embodiment of drape 224 that includes a generally conical-shaped drape upper portion 283 that extends from sheath side wall 276 to the drape lower portion 285. The drape lower portion 285 then extends in a cylindrical manner (i.e., parallel sidewalls) along drape sides 294. Although drape lower portion 285 is shown and described as extending linearly and cylindrically, drape lower portion 285 may extend in other manners with varied sizes and shapes, and may include a closure (not shown), such as a drawstring, elastic band, etc. at the second end 287.

As shown in FIG. 20, drape lower portion 285 extends over reader 120 and a length of cord(s) 267. In this manner, drape 224 can provide a sterile barrier that extends for several feet, for example six feet, to allow reader 120 to be situated adjacent to a patient during an implant procedure. In at least some embodiments, drape 224 may extend to cover additional components connected to reader 120. Fasteners, such as tie strap 299, can be used to secure the drape lower portion 285, which can substantially limit or prevent air exchange between reader 120 and environmental air outside sheath 222 and drape 224, as shown in FIG. 20. The extended drape lower portion 285 allows for positioning of reader 120 adjacent to the patient, which allows an assistant to scan objects 161 (i.e., implants) and pass them directly to a surgeon for implantation as quickly and efficiently as possible, and without leaving the near proximity of the surgeon.

Figure 25:
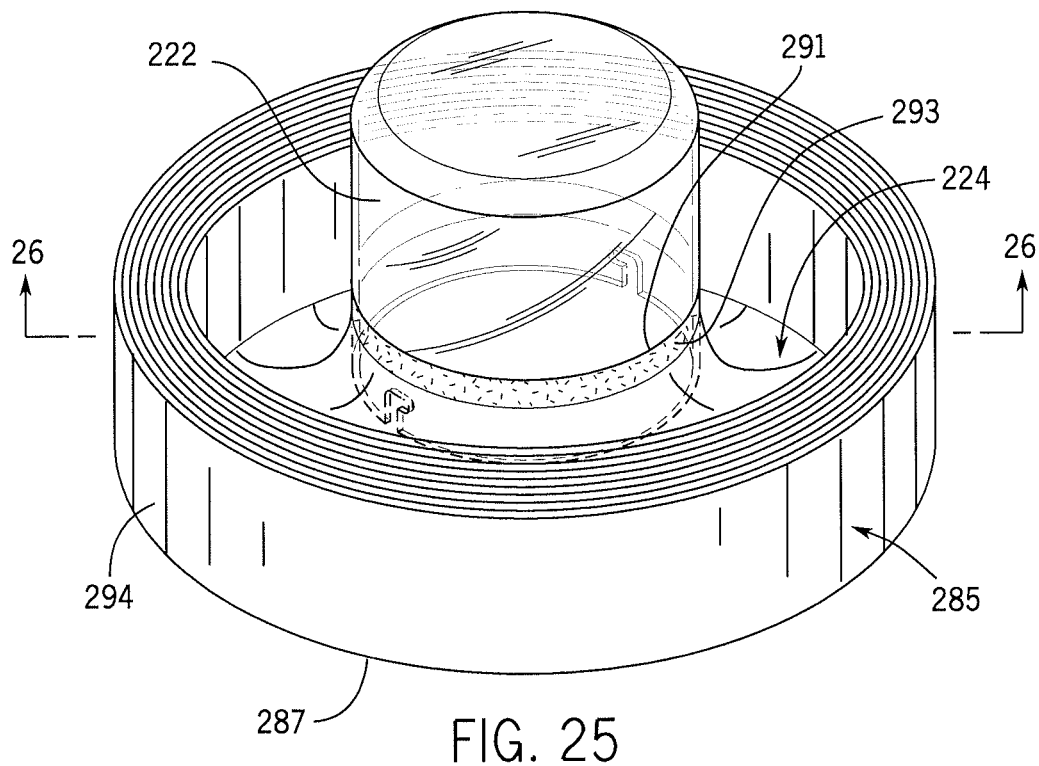
FIG. 25 is a perspective view of the sheath and drape of FIG. 20, in an exemplary folded configuration.
Figure 26:
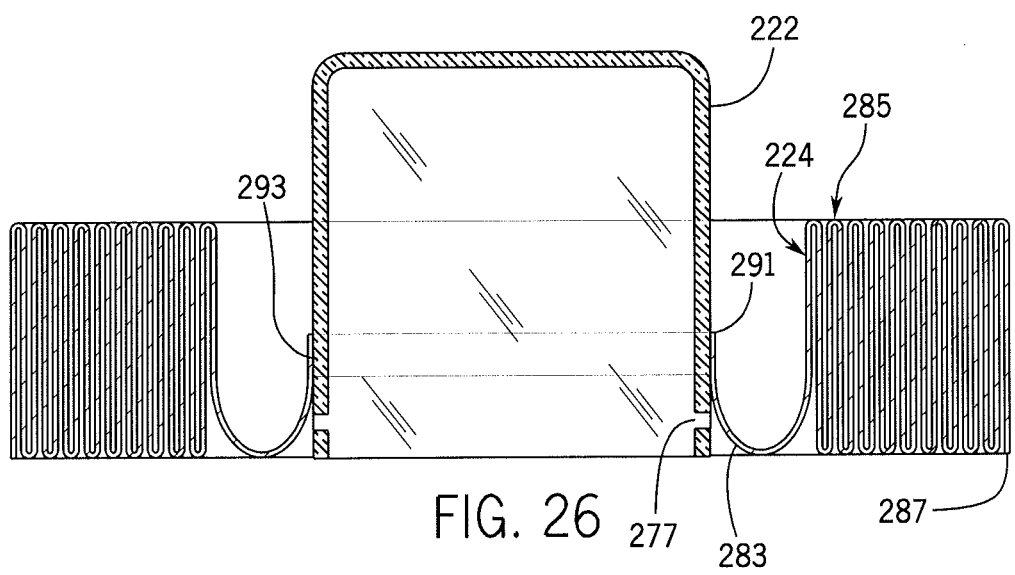
FIG. 26 is a sectional side view taken at line 26-26 of FIG. 25.

Referring to FIGS. 25 and 26, FIG. 25 illustrates a perspective view of sheath 222 and medical drape 224 of FIG. 20, in a rolled configuration, and FIG. 26 illustrates a sectional side view taken at line 25-25 of FIG. 25. Prior to installation of sheath 222 and drape 224, drape 224 is situated in a folded configuration, such as a telescopic fold, to facilitate convenient and efficient installation of over reader 120 and cord(s) 267. To install sheath 222 and drape 224, the user places the sheath 222 and the folded drape 224 over reader 120 to position the sheath 222 onto cover 133. The sheath 222 is interlocked with cover 133 and the drape 224 is then unfolded over the reader 120 and the cord(s) 267. In FIG. 25, drape 224 is shown in a folded configuration having circular shape. Depending on the shape of the drape 224, particularly, the drape lower portion 285, the drape 224 may have a non-circular or partially circular shape when folded, such as in a square configuration.

As one skilled in the art would understand, a medical implant of the present disclosure includes implants, such as artificial joints, spinal implants, active medical device implants such as cardiac defibrillators, cardiac pacemakers, gastrointestinal pace makers, and arterial stents, as well as other passive or active implantable medical devices. In addition to implants, tracking assembly 10, 110, and 210 can be utilized to scan other medical devices and/or instruments that may be used during surgery, such as a clamp, a scalpel, etc.

The present disclosure includes the following embodiments:

An assembly for tracking implants comprising
  a reader comprising:
    a scanner,
    a housing structure comprising
      a cover comprising
        an aperture on a top surface of the cover, and
      a base comprising
        an inset groove to receive the cover, and
    optionally a transparent sterile sheath having a top surface and side walls, wherein the transparent sterile sheath encases the cover of the housing structure,
    wherein the scanner is positioned to form a focal point above the aperture,
    wherein the scanner is enclosed in the housing structure;
  a medical drape attached to the side walls of the transparent sterile sheath; and
  a computer in communication with the reader.

The assembly wherein the reader further comprises an LED and a scanner mounting structure supporting the scanner and LED device wherein the scanner mounting structure is attached to the base.

An assembly for tracking implants comprising
  a handheld reader;
  a housing structure comprising
    a cover comprising
      an aperture on a top surface of the cover, and
    a base comprising
      an inset groove to receive the cover;
  optionally a transparent sterile sheath having a top surface and side walls,
    wherein the transparent sterile sheath encases the cover of the housing structure,
    wherein the handheld reader is secured to the base to form a focal point above the aperture,
    wherein the handheld reader is enclosed in the housing structure;
  a medical drape attached to the side walls of the transparent sterile sheath; and a computer in communication with the handheld reader.

A reader comprising:
  a scanner;
  an LED;
  a scanner mounting structure supporting the scanner and LED;
  a housing structure comprising
    a cover comprising
      an aperture on a top surface of the cover, and
    a base comprising
      a top surface to receive the scanner mounting structure,
      an inset groove to receive the housing structure; and
  an optional transparent sterile sheath encasing the cover of the housing structure,
  wherein the scanner mounting structure is attached to the base
  wherein the scanner and LED are positioned to form a focal point above the aperture,
  wherein the scanner, LED and mounting structure are enclosed in the housing structure.

The reader wherein the cover further comprises at least one radial pin extending from a side surface of the cover.

The reader wherein the cover further comprises at least one pin hole in the side of the cover to receive a vertical pin.

The reader wherein the base further comprises at least one vertical pin extending up through the inset groove.

The reader of claim 4 wherein the base further comprises an inset channel extending radially from the scanner mounting structure to the edge of the top surface of the base, and a removable channel cover.

The reader having a transparent sterile sheath covering the cover of the reader.

The reader having a transparent sterile sheath covering the cover of the reader wherein the transparent sterile sheath further comprises at least one radial pin slot to receive the radial pin from the cover.

The reader wherein the scanner is capable of scanning 2×2 mil etched identifiers.

The reader wherein the top surface of the transparent sheath in the area above the aperture of the cover corresponds with the focal point of the scanner and LED.

The reader further comprising a medical drape wherein the medical drape does not obstruct the aperture of the housing structure and wherein the medical drape extends radially out from the side surface of the housing structure.

The reader wherein the transparent sterile sheath has magnifying abilities.

The reader wherein the transparent sterile sheath is formed of a single piece of transparent plastic.

The reader wherein the transparent sterile sheath is disposable.

A method of using a reader comprising the steps of:
providing a reader comprising:
 a scanner;
 an LED;
 a scanner mounting structure supporting the scanner and LED device; and
 a housing structure comprising
  a cover comprising
  an aperture on a top surface of the cover, and
  a base comprising
  a top surface to receive the scanner mounting structure,
  an inset groove to receive the housing structure,
 wherein the scanner mounting structure is attached to the base
 wherein the scanner and LED are positioned to form a focal point above the aperture,
 wherein the scanner, LED and mounting structure are enclosed in the housing structure;
placing a transparent sterile sheath over the housing structure of the reader;
placing an implant having an identifier onto the top surface of the transparent sterile sheath above the aperture; and
scanning the identifier of the implant to electronically record the stored data.

The method further comprising the step of positioning a medical drape to cover the remaining portions of a reader.

The method wherein the identifier on the implant is an etched 2×2 matrix containing data regarding the implant.

The method wherein positioning the medical drape to cover the remaining portions of a reader device comprises unrolling the medical drape from the transparent sterile sheath to extend the medical drape around the remaining portions of the reader device.

A tracking assembly comprising:
 a reader comprising:
  a housing structure that includes a base and a cover;
  a scanner having a scanner housing, where the scanner housing is at least partially positioned in a cavity provided in the base; and
  an aperture provided in the cover, where the cover is configured to receive a transparent sterile sheath to at least partially encase the cover.

The assembly further comprising a transparent sterile sheath positioned over the cover.

The assembly further comprising a medical drape attached to a side wall of the transparent sterile sheath.

The assembly where the medical drape extends radially and downwardly from the transparent sterile sheath.

The assembly where the medical drape is removably secured to the transparent sterile sheath by an elastic band.

The assembly where the medical drape is permanently secured to the transparent sterile sheath.

The assembly where the combination of the transparent sterile sheath and the medical drape substantially cover the housing structure to substantially limit exposure of the housing structure to the atmosphere.

The assembly where the scanner is positioned in the base to form a focal point on a top surface of the transparent sterile sheath above the aperture.

The assembly where the reader further comprises a scanner mounting structure supporting the scanner wherein the scanner mounting structure is positioned substantially in the cavity and secured to the base.

The assembly where the scanner is in communication with a computer device located apart from the reader, where the computer device is capable of receiving and storing information obtained from the identifier upon being scanned by the reader.

The assembly where the scanner is capable of scanning 2×2 mm etched identifiers.

A tracking assembly comprising:
 a reader comprising:
  a scanner;
  a scanner mounting structure supporting the scanner;
  a housing structure that includes a cover with an aperture on a top surface of the cover and a base secured to the cover,
  where the housing structure is configured to receive a one or more coverings to at least partially enclose the housing structure,
  where the scanner mounting structure is secured to the base, and
  where the scanner and scanner mounting structure are substantially enclosed in the housing structure.

The assembly where the one or more coverings includes a transparent sterile sheath positioned over the cover.

The assembly where the one or more coverings further includes a medical drape attached to a side wall of the transparent sterile sheath.

The assembly further including a cavity positioned inside the base, where the scanner is substantially positioned inside the cavity.

The assembly where the scanner includes a scanner housing attached to the scanner mounting structure.

The assembly where the one or more coverings includes a transparent sterile sheath and a medical drape.

The assembly where the one or more coverings includes a transparent sterile sheath and a medical drape attached to a side wall of the transparent sterile sheath.

The assembly where the scanner is capable of scanning 2×2 mm etched identifiers.

The assembly where a top surface of the transparent sheath in an area above the aperture of the cover corresponds with the focal point of the scanner.

The assembly where the scanner housing has a lens secured thereto, where the lens includes a front surface, where the front surface is situated between about 3 inches to about 5 inches from the aperture of the cover.

The assembly where the transparent sterile sheath includes a sheath top surface having at least one of a convex portion and a magnifying portion.

The assembly where the transparent sterile sheath is formed of a single piece of transparent plastic.

The assembly where the transparent sterile sheath is disposed of after identifiers have been received for all the medical implants implanted in a single patient during an operation.

The assembly where the sheath is rigid and cylindrical in shape.

The assembly where the sheath is cylindrical in shape and includes a locking mechanism.

The assembly where the base of the reader includes a diameter that extends between about 6 inches to about 10 inches.

The assembly where the scanner is connected via a cord to a computer located outside the housing structure.

A method of using a tracking assembly comprising the steps of:
  providing a tracking assembly comprising:
    a reader comprising:
      a scanner;
      a scanner mounting structure supporting the scanner;
      a housing structure comprising:
        a cover comprising:
          an aperture on a top surface of the cover; and
        a base secured to the cover, where the base includes a cavity;
      where the scanner mounting structure is positioned in the cavity of the base, and where the scanner and scanner mounting structure are substantially enclosed in the housing structure;
  covering the cover with a transparent sterile sheath;
  placing an implant having an identifier over the aperture; and
  scanning the identifier of the implant to electronically record the implant data.

The method further including attaching a medical drape to the transparent sterile sheath.

The method where the identifier on the implant is an etched 1.4×1.4 mm matrix containing data regarding the implant.

The method further including sensing an implant having an identifier, when the implant is positioned above the aperture and automatically obtaining a scan of the identifier.

A tracking assembly comprising:
  a reader comprising:
    a housing structure that includes a base and a cover; and
    a scanner positioned in the housing structure for scanning a medical implant;
  a sterile sheath positioned on the cover; and
  a sterile drape secured to the sterile sheath, where the sterile drape and the sterile sheath substantially enclose the housing structure.

The assembly where the sterile drape is permanently secured to the sterile sheath.

The assembly where the sterile drape includes a drape lower portion that at least partially encloses one or more cords extending from the housing structure.

The assembly where the sterile drape extends radially and downwardly from the sterile sheath.

The assembly where the sterile drape is removably secured to the sterile sheath.

The assembly where the permanent securement of the drape to the sterile sheath provides an airtight seal therebetween.

The assembly further comprising an aperture in the cover to allow optical signals to pass between the scanner and the medical implant.

The assembly where the scanner is positioned in the base to form a focal point on a top surface of the sterile sheath above the aperture.

The assembly where the base further comprises a cavity for at least partially receiving the scanner.

The assembly where the scanner is in communication with a computer device located apart from the reader, where the computer device is capable of receiving and storing information obtained from the medical implant upon being scanned by the reader.

The assembly where the sterile sheath is formed of a single piece of transparent plastic.

A tracking assembly comprising:
  a reader comprising:
    a scanner;
    a scanner mounting structure supporting the scanner;
    a housing structure that includes a cover with an aperture and a base secured to the cover,
    a sheath positioned on the cover; and
    a drape permanently secured to the sterile sheath, where the drape and sheath substantially enclose the housing structure,
    where the scanner mounting structure is secured to the base, and
    where the scanner and scanner mounting structure are substantially enclosed in the housing structure.

A tracking assembly comprising:
  a reader comprising:
    a scanner;
    a scanner mounting structure supporting the scanner;
    a housing structure that includes a cover with an aperture and a base secured to the cover,
    a sheath positioned on the cover; and
    a drape permanently secured to the sterile sheath along a securement band, where the drape and sheath substantially enclose the housing structure,
    where the scanner mounting structure is secured to the base, and
    where the scanner and scanner mounting structure are substantially enclosed in the housing structure.

The assembly where the drape is permanently secured to the sheath using heat to melt a portion of the drape and the sheath along the securement band to form a bond.

The assembly where the drape is permanently secured to the sheath using a chemical adhesive.

The assembly further including a cavity positioned inside the base, where the scanner is substantially positioned inside the cavity.

The assembly where the scanner includes a scanner housing attached to the scanner mounting structure.

The assembly where the scanner is capable of scanning 2×2 mm etched identifiers.

The assembly where the aperture of the cover corresponds with the focal point of the scanner.

The assembly where the sterile drape is comprised of at least one of elastomer, plastic, rubber, polyethylene, and polypropylene.

The assembly where an optically transparent portion of the sheath is situated in an area above the aperture of the cover.

The assembly where the scanner housing has a lens secured thereto, where the lens includes a front surface, where the front surface is situated between about 3 inches to about 5 inches from the aperture of the cover.

The assembly where the sterile sheath includes a sterile sheath top surface having at least one of a convex portion and a magnifying portion.

The assembly where the sterile sheath is formed of a single piece of transparent plastic.

The assembly where the sterile sheath is disposed of after identifiers have been received for all the medical implants implanted in a single patient during an operation.

The assembly where the reader is positionable adjacent to a patient during a surgical procedure.

The assembly where the scanner is connected via a cord to a computer located outside the housing structure.

A method of using a tracking assembly comprising the steps of:
- providing a tracking assembly comprising:
  - a reader comprising:
    - a scanner;
    - a scanner mounting structure supporting the scanner; and
  - a housing structure comprising:
    - a cover comprising:
      - an aperture in the cover; and
      - a base secured to the cover, where the base includes a cavity,
    - where the scanner mounting structure is positioned in the cavity of
  - the base, and where the scanner and scanner mounting structure are substantially enclosed in the housing structure;
- covering the cover with a sterile sheath and further enclosing the reader with a drape secured to the sterile sheath;
- positioning the reader adjacent to a surgical patient;
- placing an implant having an identifier over the aperture; and
- scanning the identifier of the implant to electronically record the implant data.

The method where the medical drape includes a drape upper portion and a drape lower portion, where the drape lower portion extends beyond the housing structure.

The method where further enclosing the reader with the drape further includes unfolding the drape over the housing structure and extending a lower portion over the drape to at least partially cover one or more cords extending from the housing structure.

The method further including enclosing the housing structure and all associated cords that extending therefrom, for a distance of at least four feet from the housing structure.

The method where the drape is in a telescopically folded configuration prior to unfolding over the housing structure.

Although the invention has been described with certain detail through the preceding description of the preferred embodiments, this detail is for the primary purpose of illustration. Many variations and modifications can be made by one skilled in the art without departing from the spirit and scope of the invention as described in the following claims.

What is claimed is:

1. A tracking assembly comprising:
   a reader comprising:
      a housing structure that includes a base and a cover; and
      a scanner positioned in the housing structure for scanning a medical implant;
   a sterile sheath positioned on the cover; and
   a sterile drape permanently secured to the sterile sheath, where the sterile drape and the sterile sheath substantially enclose the housing structure, and further wherein the sterile drape includes a drape lower portion that at least partially encloses one or more cords extending from the housing structure.

2. The assembly of claim 1, where the sterile drape extends radially and downwardly from the sterile sheath.

3. The assembly of claim 1, where the sterile drape is removably secured to the sterile sheath.

4. The assembly of claim 1, where the sterile drape is comprised of at least one of elastomer, plastic, rubber, polyethylene, and polypropylene.

5. The assembly of claim 1, further comprising an aperture in the cover to allow optical signals to pass between the scanner and the medical implant.

6. The assembly of claim 5, where the scanner is positioned in the base to form a focal point on a surface of the sterile sheath positioned above the aperture.

7. The assembly of claim 6, where the base further comprises a cavity for at least partially receiving the scanner.

8. The assembly of claim 1, where the scanner is in communication with a computer device located apart from the reader, where the computer device is capable of receiving and storing information obtained from a medical implant upon being scanned by the reader.

9. The assembly of claim 1, where the sterile sheath is formed of a single piece of transparent plastic.

10. A tracking assembly comprising:
    a reader comprising:
       a scanner;
       a scanner mounting structure supporting the scanner;
       a housing structure that includes a cover with an aperture and a base secured to the cover;
       a sheath positioned on the cover; and
       a drape permanently secured to the sterile sheath, where the drape and sheath substantially enclose the housing structure,
       where the scanner mounting structure is secured to the base, and
       where the scanner and scanner mounting structure are substantially enclosed in the housing structure.

11. The assembly of claim 10, where the sheath is rigid and cylindrical in shape.

12. The assembly of claim 10, where the sheath is cylindrical in shape and includes a locking mechanism.

13. The assembly of claim 10, further including a cavity positioned inside the base, where the scanner is substantially positioned inside the cavity.

14. The assembly of claim 10, where the scanner includes a scanner housing attached to the scanner mounting structure.

15. The assembly of claim 14, where the scanner is capable of scanning 2×2 mm etched identifiers.

16. The assembly of claim 10, where the aperture of the cover corresponds with a focal point of the scanner.

17. The assembly of claim 16, where an optically transparent portion of the sheath is situated in an area above the aperture of the cover.

18. The assembly of claim 14, where the scanner housing has a lens secured thereto, where the lens includes a front surface, where the front surface is situated between about 3 inches to about 5 inches from the aperture of the cover.

19. The assembly of claim 16, where the sterile sheath includes a sterile sheath top surface having at least one of a convex portion and a magnifying portion.

20. The assembly of claim 10, where the sterile sheath is formed of a single piece of transparent plastic.

21. The assembly of claim 10, where the sterile sheath is disposed of after identifiers have been received for all the medical implants implanted in a single patient during an operation.

22. The assembly of claim 10, where the scanner is connected via a cord to a computer located outside the housing structure.

23. A method of using a tracking assembly comprising the steps of:
   providing a tracking assembly comprising:
      a reader comprising:
         a scanner;
         a scanner mounting structure supporting the scanner; and
         a housing structure comprising:
            a cover comprising:
               an aperture in the cover; and
               a base secured to the cover, where the base includes a cavity,
      where the scanner mounting structure is positioned in the cavity of the base, and where the scanner and scanner mounting structure are substantially enclosed in the housing structure;
   covering the cover with a sterile sheath and further enclosing the reader with a drape secured to the sterile sheath, where the sterile drape and the sterile sheath substantially enclose the housing structure, and further wherein the sterile drape includes a drape lower portion that at least partially encloses one or more cords extending from the housing structure;
   positioning the reader adjacent to a surgical patient;
   placing an implant having an identifier over the aperture; and
   scanning the identifier of the implant to electronically record the implant data.

\* \* \* \* \*